US012246097B2

(12) United States Patent
Irvine et al.

(10) Patent No.: US 12,246,097 B2
(45) Date of Patent: *Mar. 11, 2025

(54) NANOPARTICLE VACCINE ADJUVANT AND METHODS OF USE THEREOF

(71) Applicants: Massachusetts Institute of Technology, Cambridge, MA (US); La Jolla Institute for Immunology, La Jolla, CA (US)

(72) Inventors: Darrell J. Irvine, Arlington, MA (US); Murillo Silva, Lancaster, MA (US); Shane Crotty, San Diego, CA (US); Yu Kato, San Diego, CA (US)

(73) Assignees: MASSACHUSETTS INSTITUTE OF TECHNOLOGY, Cambridge, MA (US); LA JOLLA INSTITUTE FOR IMMUNOLOGY, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/151,182

(22) Filed: Jan. 6, 2023

(65) Prior Publication Data

US 2023/0157967 A1 May 25, 2023

Related U.S. Application Data

(63) Continuation of application No. 16/510,463, filed on Jul. 12, 2019, now Pat. No. 11,547,672.

(60) Provisional application No. 62/731,214, filed on Sep. 14, 2018.

(51) Int. Cl.
| *A61K 9/51* | (2006.01) |
| *A61K 9/00* | (2006.01) |
| *A61K 9/14* | (2006.01) |
| *A61K 9/19* | (2006.01) |
| *A61K 39/00* | (2006.01) |
| *A61K 39/02* | (2006.01) |
| *A61K 39/39* | (2006.01) |
| *A61K 47/69* | (2017.01) |
| *B82Y 5/00* | (2011.01) |
| *B82Y 40/00* | (2011.01) |

(52) U.S. Cl.
CPC ............ *A61K 9/51* (2013.01); *A61K 9/0019* (2013.01); *A61K 9/141* (2013.01); *A61K 9/19* (2013.01); *A61K 39/02* (2013.01); *A61K 39/39* (2013.01); *A61K 39/4611* (2023.05); *A61K 39/4612* (2023.05); *A61K 39/4622* (2023.05); *A61K 39/464402* (2023.05); *A61K 39/464838* (2023.05); *A61K 2039/55555* (2013.01); *A61K 2039/55572* (2013.01); *A61K 2239/31* (2023.05); *B82Y 5/00* (2013.01); *B82Y 40/00* (2013.01)

(58) Field of Classification Search
None
See application file for complete search history.

(56) References Cited

U.S. PATENT DOCUMENTS

| 3,238,190 | A | 3/1966 | Erbring |
| 4,912,094 | A | 3/1990 | Myers |
| 5,057,540 | A | 10/1991 | Kensil |
| 8,283,456 | B2 | 10/2012 | Gin |
| 9,107,904 | B2 | 8/2015 | Irvine |
| 9,149,520 | B2 | 10/2015 | Walker |
| 9,241,988 | B2 | 1/2016 | Shaw |
| 2005/0220814 | A1 | 10/2005 | Dominowski |
| 2011/0206758 | A1 | 8/2011 | Vandepapeliere |
| 2011/0300177 | A1 | 12/2011 | Gin |
| 2014/0356384 | A1 | 12/2014 | Hubbell |
| 2016/0045595 | A1 | 2/2016 | Morein |

FOREIGN PATENT DOCUMENTS

| EP | 0362278 | 4/1990 |
| EP | 0362279 | 4/1990 |
| WO | 9414454 | 7/1994 |
| WO | 9633739 | 10/1996 |
| WO | 9836772 | 8/1998 |
| WO | 2009156960 | 12/2009 |
| WO | 2018104313 | 6/2018 |
| WO | 2019051149 | 3/2019 |

OTHER PUBLICATIONS

Fox et al. A nanoliposome delivery system to synergistically trigger TLR4 and TLR7. Journal of Nanobiotechnology 2014, 12:17.*
Bach, et al., "The effect of infections on susceptibility to autoimmune and allergic diseases", N. Eng. J. Med., 347:911-20 (2002).
Bodera, "Immunostimulatory oligonucleotides", Recent Pat. Inflamm. Allergy Drug Discov., 5(1):87-93 (2011).
Carrasco, et al., "B cells acquire particulate antigen in a macrophage-rich area at the boundary between the follicle and the subcapsular sinus of the lymph node", Immunity, 27(1):160-171 (2007).
Dalpke, "Phosphodiester CpG oligonucleotides as adjuvants: polyguanosine runs enhance cellular uptake and improve immunostimulative activity of phosphodiester CpG oligonucleotides in vitro and in vivo", Immunology, 106(1): 102-12 (2002).
Dalsgaard, et al. "Saponin adjuvants. 3. Isolation of a substance from Quillaja saponaria Molina with adjuvant activity in food-and-mouth disease vaccines," Archiv. Gesamte Virusforsch, 44:243-54 (1974).

(Continued)

*Primary Examiner* — Nianxiang Zou
(74) *Attorney, Agent, or Firm* — PABST PATENT GROUP LLP

(57) ABSTRACT

Non-liposome, non-micelle particles formed of a lipid, an additional adjuvant such as a TLR4 agonist, a sterol, and a saponin are provided. The particles are porous, cage-like nanoparticles, also referred to as nanocages, and are typically between about 30 nm and about 60 nm. In some embodiments, the nanocages include or are administered in combination with an antigen. The particles can increase immune responses and are particularly useful as adjuvants in vaccine applications and related methods of treatment. Preferred lipids, additional adjuvants including TLR4 agonists, sterols, and saponins, methods of making the nanocages, and method of using them are also provided.

20 Claims, 19 Drawing Sheets

(56) References Cited

OTHER PUBLICATIONS

Deuwell, et al., "ISCOMATRIX adjuvant combines immune activation with antigen delivery to dendritic cells in vivo leading to effective cross-priming of CD8+ T cells", J Immunology. 187(1):55-63 (2011).
Ersching, et al., "Germinal Center Selection and Affinity Maturation Require Dynamic Regulation of mTORC1 Kinase", Immunity, 46(6):1045-58 (2017).
Fiedler, "Further constituents of Crataegus; paper-chromatographic determination of chlorogenic and caffeic acid", Arzneimittel-Forsch. 4:41-5 (1954).
Fousteri, et al., "Subcutaneous insulin B: 9-23/IFA immunisation induces Tregs that control late-stage prediabetes in NOD mice through IL-10 and IFNgamma", Diabetologia, 53:1958-70 (2010).
Gitlin, et al, "Humoral Immunity. T cell help controls the speed of the cell cycle in germinal center B cells", Science, 349(6248):643-6 (2015).
Gitlin, et al., "Clonal selection in the germinal center by regulated proliferation and hypermutation", Nature, 509(7502):637-40 (2014).
Hartmann, "Delineation of a CpG Phosphorothioate oligodeoxynucleotide for activating primate immune responses in vitro and in vivo", J. of Immun., 164(3):1617-24 (2000).
International Search Report for corresponding PCT application PCT/US2019/041580 dated Dec. 6, 2019.
Ito, et al., "Cancer Neoantigens: A Promising Source of Immunogens for Cancer Immunotherapy" J. Clin. Cell Immunol., 6:322 (2015).
Johnson, et al., "Characterization of a nontoxic monophosphoryl lipid A", Rev. Infect. Dis., 9 Suppl: S512-S516 (1987).
Kayagaki, et al., "Noncanonical Inflammasome activation by intracellular LPS independent of TLR4", Science, 241(6151): 1246-1249 (2013).
Liu, et al., "Structure-based programming of lymph-node targeting in molecular vaccines", Nature Letters, 507:519-22 (+ 11 pages of extended data) (2014).
Livingston, "Large Scale Synthesis of the Next Generation Synthetic Saponin Adjuvant TiterQuil", National Institutes of Health, accessed Sep. 11, 2018.
Luderitz, et al., "Structural relationship of *Salmonella* O and R antigens", Ann. N. Y. Acad. Sci., 133:349-74 (1966).
Mascola, et al., "HIV-1 neutralizing antibodies: understanding nature's pathways", Immunological reviews, 254(1):225-44 (2013).
Morelli, "Development of prophylactic and therapeutic vaccines using the ISCOMATRIX adjuvant", Immunology and Cell, 87(5):371-6 (2009).
Morelli, et al., "ISCOMATRIX: a novel adjuvant for use in prophylactic and therapeutic vaccines against infectious diseases", J. Med. Microbiol., 61(Pt 7):935-43 (2012).
Phan, et al., "Immune complex relay by subcapsular sinus microphages and noncognate B cells drives antibody affinity maturation", Nat. Immunol., 10(7):786-793 (2009).
Phan, et al., "Subcapsular encounter and complement-dependent transport of immune complexes by lymph node B cells", Nat. Immunol., 8(9):992-1000 (2007).
Ragupathi, et al., "Natural and synthetic Saponin adjuvant QS-21 for vaccines against cancer", Expert Rev. Vaccines, 10(4): 463-70 (2011).
Ramirez-Ortiz, Zaida G., et al., "Toll-Like Receptor 9-Dependent Immune Activation by unmethylated CpG Motifs in Aspergillus fumigatus DNA", Infection and Immunity, 2123-2129 (2008).
Schumacher et al., "Neoantigens in cancer immunotherapy", Science, 348(6230):69-74 (2015).
Shi, et al., "Inflammatory caspases are innate immune receptors for intracellular LPS", Nature, 514(7521): 187-192 (2014).
Silva, et al., "The Combination of ISCOMATRIX Adjuvant and TLR Agonists Induces Regression of Established Solid Tumors In Vivo", J Immunol., 194(5):2199-207 (2015).
Silveira, et al., "Quillaja brasiliensis saponins are less toxic than Quil A and have similar properties when used as an adjuvant for a viral antigen preparation", Vaccine, 29:9177-82 (2011).
Sun, et al., "ISCOMs and ISCOMATRIX", Vaccine, 27(33):4388-401 (2009).
Vochten, et al., "Physico-chemical properties of sapoalbin and their relation to the foam stability", J. Pharm. Belg., 42:213-26 (1968).
Vollmer and Krieg, "Immunotherapeutic applications of CpG oligodeoxynucleotide TLR9 agonists", Adv. Drug Deliv Rev, 61(3): 195-204 (2009).
Weiner, "Immunostimulatory oligodeoxynucleotides containing the CpG motif are effective as immune adjuvants in tumor antigen immunization", PNAS, 94(20): 10833-7 (1997).
What are The Differences Between Liposomes And Micelles?, downloaded online Mar. 29, 2022 from Website of Avanti Polar Lipids.
Wilson, et al., "Inflammasome-Dependent and -Independent IL-18 Production Mediates Immunity to the ISCOMATRIX Adjuvant", J. Immunol., 192(7):3259-68 (2014).
Yoshikawa, et al., "Bioactive saponins and glycosides. III. Horse chestnut. (1): The structures, inhibitory effects on ethanol absorption, and hypoglycemic activity of escins Ia, Ib, IIa, IIb, and IIIa from the seeds of *Aesculus hippocastanum* L", Chem. Pharm. Bull (Tokyo) Aug. 44(8): 1454-64 (1996).
Zaida, et al., "Toll-like receptor 9-dependent immune activation by unmethylated CpG motifs in Aspergillus fumigatus DNA", Infect. Immun., 76(5):2123-9, (2008).
Zu, et al., "Recent Development in the Synthesis of Natural Saponins and Their Derivatives", J. Carb. Chem., 33(6):269-97 (2014).

\* cited by examiner

Labeled 70kDa dextran
w/PBS or Saponin-
MPLA NP                          Flow cytometry 0hr                              4hr

US 12,246,097 B2

NANOPARTICLE VACCINE ADJUVANT AND METHODS OF USE THEREOF

CROSS-REFERENCE TO RELATED APPLICATION

This application is a continuation of U.S. application Ser. No. 16/510,463, filed Jul. 12, 2019, which claims the benefit of and priority to U.S. Ser. No. 62/731,214, filed Sep. 14, 2018, which are specifically incorporated by reference herein in their entireties.

STATEMENT REGARDING FEDERALLY SPONSORED RESEARCH

This invention was made with Government support under Grant Nos. UM1 AI100663 and R01 AI125068 awarded by the National Institutes of Health. The Government has certain rights in the invention.

FIELD OF THE INVENTION

This invention relates to the field of vaccine technology and more specifically to adjuvants that can be used to increase immune responses against an antigen.

BACKGROUND OF THE INVENTION

Adjuvants are often added to vaccine formulations to modify the immune response. For example, adjuvants can lead to a higher amount of antibodies and a longer-lasting protection, thus minimizing the amount of injected antigen used. Adjuvants may also be used to enhance the efficacy of a vaccine by helping to modify the immune response to particular types of immune system cells. For example, certain adjuvants can favor T cells activation over antibody-secreting B cells activation depending on the purpose of the vaccine.

Immunostimulatory complexes called ISCOMs are particulate antigen delivery systems having antigen, cholesterol, phospholipid and saponin (Quil A or other saponin) with potent immunostimulatory activity. ISCOMATRIX® is a particulate adjuvant having cholesterol, phospholipids and saponins (Quil A) but without containing antigen. See, e.g., U.S. Pat. No. 9,149,520, Sun, et al., Volume 27, Issue 33, 16 Jul. 2009, Pages 4388-4401, and Morelli, et al., J Med Microbiol. 2012 July; 61(Pt 7):935-43. doi: 10.1099/jmm.0.040857-0. Epub 2012 Mar. 22. This adjuvant has principally the same structure as ISCOMs, consisting of perforated cage-like particles of approximately 40 nm in diameter. The antigens can be formulated with ISCOMATRIX® to produce vaccines capable of antigen presentation and immunostimulants similar to ISCOMs-type formulations, but with a wider range of applicability, since its use is not limited to hydrophobic membrane proteins. Modifications of ISCOMs formulations and ISCOMATRIX® have also been developed to achieve a better association of some antigens, such as described in WO 98/36772.

ISCOMs and ISCOMATRIX® combine the advantages of a particulate delivery system with the in situ presence of an adjuvant (Quil A) and consequently have been found to be more immunogenic than other colloidal systems such as liposomes and protein micelles. Formulations of ISCOMs and ISCOMATRIX® retained the adjuvant activity of the Quil A, while increasing its stability, reducing its hemolytic activity, and producing less toxicity. They also generate a similar immune response to the one obtained by immunizing with simple mixtures of antigen and saponin, but allow for the use of substantially smaller amounts of antigen. Several ISCOMs-type vaccine formulations or containing ISCOMATRIX® have been approved for veterinary use, for example against equine influenza virus.

Other liposomal systems mainly composed of saponins from *Q. saponaria* and sterols (primarily cholesterol) have been described, one of which is referred to as ASO1B. See, e.g., WO 96/33739, also being formulated as emulsions such as described in US 2005/0220814. See, also, U.S. Published Application No. 2011/0206758.

Iscomatrix-like adjuvants such as ISCOMATRIX® are thought to function via canonical inflammasome activation and subsequent release of pro-inflammatory cytokines such as IL-18 and IL-10 (Wilson, et al., *Journal of immunology*. 2014; 192(7):3259-68. doi: 10.4049/jimmunol.1302011. PubMed PMID: 24610009). This mechanism is thought to be mediated at least in-part by endosomal degradation and the release of NRLP3-activating cathepsin proteases into the cytosol. Despite the promising results obtained with this adjuvant, there remains a need for even stronger adjuvants preferably with reduced toxicity.

Thus, it is an object of the invention to provide improved adjuvants, vaccine formulations formed therewith, and methods of use thereof.

SUMMARY OF THE INVENTION

Non-liposome, non-micelle particles formed of a lipid, an additional adjuvant such as a TLR4 agonist, a sterol, and a saponin are provided. The particles can increase immune responses and are particularly useful as adjuvants in vaccine applications and other methods of treatment.

The particles are porous or perforated cage-like nanoparticles, also referred to herein as nanocages. The particles are typically between about 30 nm and about 60 nm. The particles can also include an antigen incorporated or encapsulated therein. In some embodiments, the particles do not include antigen. However, antigen, for example free, unincorporated antigen can form part of the same or a different pharmaceutical composition and be used in combination with the adjuvant particles as a vaccine.

Suitable ratios for the lipid, additional adjuvant (e.g., TLR4 agonist), sterol, and saponin components are provided. For example, in a particular embodiment, the lipid: additional adjuvant (e.g., TLR4 agonist):sterol:saponin are in a molar ratio of 2.5:1:10:10, or a variation thereof wherein the molar ratio of any one or more of the lipid, additional adjuvant, sterol, and/or saponin is increased or decreased by any value greater than 0 and up to about 3.

Exemplary lipids, additional adjuvants including TLR4 agonists, sterols, and saponins are also provided. The lipid is typically a phospholipid, such as 2-dipalmitoyl-sn-glycero-3-phosphocholine (DPPC). The sterol is most typically cholesterol or a derivative thereof. The saponin can be a natural or synthetic saponin, for example, Quil A or submixture or pure saponin separated therefrom. In particular embodiments, the saponin is a natural or synthetic Q-21, or an analog thereof.

Preferred additional adjuvants are TLR4 agonists. An exemplary TLR4 agonist is a lipopolysaccharide (LPS) or a lipid A derivative thereof. In particular embodiments, the lipid A derivative is a monophosphoryl lipid A such as a 4'-monophosporyl lipid A (MPLA) or 3-O-deacylated monophosphoryl lipid A (3D-MPLA).

Other additional adjuvants include, for example, pathogen-associated molecular patterns (PAMPs). In some embodiments, the PAMP is a TLR ligand, a NOD ligand, an RLR ligand, a CLR ligand, an inflammasome inducer, a STING ligand, or a combination thereof. Typically, the additional adjuvant includes a lipid to facilitate incorporation of the adjuvant into the nanocage during self-assemble. Thus, any additional adjuvant, and particularly those that do not already include one, can be modified to include a lipid.

In a specific embodiment, the lipid is DPPC, the additional adjuvant is a natural or synthetic MPLA, the sterol is cholesterol, and the saponin is Quil A in a molar ratio of 2.5:1:10:10.

Methods of making the particles are also provided. The methods typically include mixing the lipid, additional adjuvant (e.g., TLR4 agonist), sterol, and saponin in an aqueous carrier including detergent to form a solution and removing the detergent until the lipid, additional adjuvant (e.g., TLR4 agonist), sterol, and saponin self-assemble into porous or perforated, cage-like nanoparticles. The detergent can be removed by, for example, dialysis. The particles can be separated or purified from free, unassembled components and/or non-nanocage structures such liposomes and micelles. Typically, the disclosed methods lead to a monodispersion of particles in the size range of about 30 nm to about 60 nm.

Pharmaceutical compositions including a plurality of particles, a pharmaceutical carrier, and optionally antigen are also provided. The composition typically includes an effective amount of the nanocage particles alone or in combination with antigen to increase an immune response in a subject in need thereof. The immune response can be, for example, increasing an antigen-specific antibody response, increasing a response in a germinal center, increasing plasmablast frequency, increasing inflammatory cytokine, increasing drainage of antigen from an injection site, increasing antigen accumulation in a lymph node, increasing permeability of a lymph node, increasing lymph flow, increasing antigen-specific B cell antigen uptake in a lymph nodes, increase a humeral response beyond the proximal lymph node, increase diffusion of antigen into B cell follicles, or a combination thereof.

The particles can increase the immune response relative to a control such as the absence of the particles, and/or the presence of another adjuvant such as Addavax, alum, particles having the same formulation absent the additional adjuvant (e.g., TLR4 agonist), or a liposome or micelle formulation having the same lipid, additional adjuvant (e.g., TLR4 agonist), sterol, and saponin. In some embodiments, the effect of the particles is improved compared to another adjuvant such as ISCOMATRIX® or ASO1B.

Methods of using the particles are also provided. For example, a method of treating a subject in need thereof can include administering the subject a pharmaceutical composition having an effective amount of particles to induce an immune response against an antigen. In some embodiments, the antigen is derived from tumor cells or a microbe, and the subject has or may develop a cancer or infection associated with the tumor cells or microbe. The methods can also include, but need not require, administering the subject an effective amount of the antigen in the same or a separate admixture (e.g., pharmaceutical composition). Preferred methods of administering particles and/or antigen include, but are not limited to, subcutaneous, intramuscular, intradermal, and intravenous injection.

Kits are also provided. An exemplary kit includes a plurality of particles in a lyophilized or dried form, or suspended in a pharmaceutically acceptable carrier. The kits can also include antigen in a lyophilized or dried form, or suspended in a pharmaceutically acceptable carrier. The particles and antigen can be packaged in a single container or separate containers. Dosage units for administration to a subject in need thereof are also provided.

DETAILED DESCRIPTION OF THE INVENTION

I. Definitions

Figure 1:
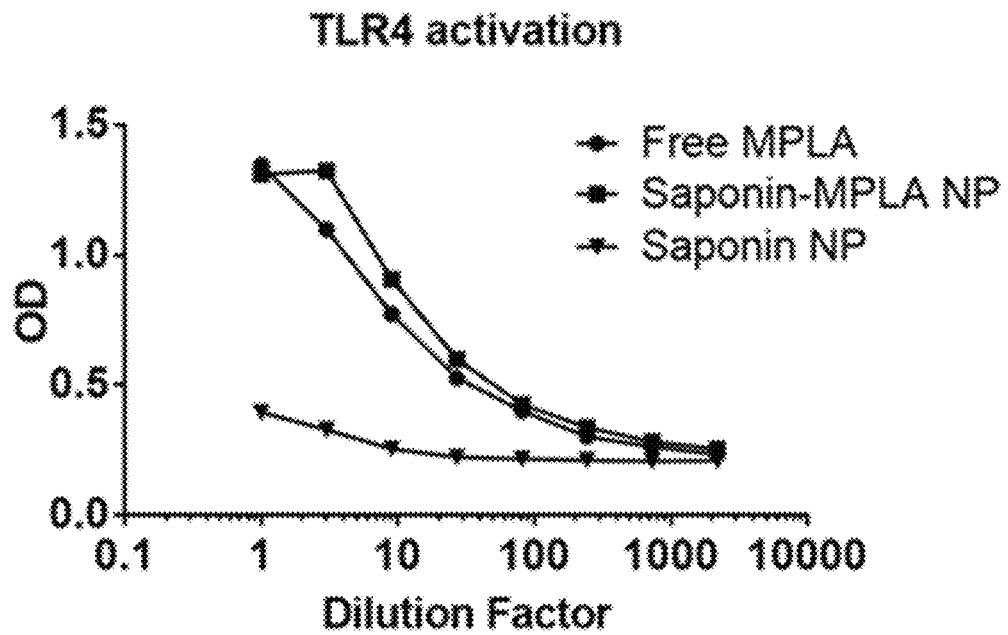
FIG. 1 is a line graph showing the results of a RAW-blue TLR4 reporter assay measuring TLR4 activation by Free MPLA, Saponin-MPLA nanoparticles (NP), and Saponin nanoparticles (NP).

As used herein, "isolated," "isolating," "purified," "purifying," "enriched," and "enriching," when used with respect to a compound of interest, indicates that the compound of interest at some point in time were separated, enriched, sorted, etc., from or with respect to other material to yield a higher proportion of the compound of interest compared to the other materials, for example, cellular material, contaminates, or active agents such as enzymes, proteins, detergent, cations, anions, or other compounds. "Highly purified," "highly enriched," and "highly isolated," when used with respect to a compound of interest, indicates that the compound of interest is at least about 70%, about 75%, about 80%, about 85%, about 90% or more, about 95%, about 99% or 99.9% or more purified or isolated from other materials such as cellular materials, contaminates, or active agents such as enzymes, proteins, detergent, cations or anions. "Substantially isolated," "substantially purified," and "substantially enriched," when used with respect to a compound of interest, indicates that the compound of interest is at least about 70%, about 75%, or about 80%, more usually at least 85% or 90%, and sometimes at least 95% or more, for example, 95%, 96%, and up to 100% purified or isolated from other materials, such as cellular materials, contaminates, or active agents such as enzymes, proteins, detergent, cations or anions.

As used herein, the term "immune cell" refers to cells of the innate and acquired immune system including neutrophils, eosinophils, basophils, monocytes, macrophages, dendritic cells, lymphocytes including B cells, T cells, and natural killer cells.

As used herein, the term "immune tolerance" as used herein refers to any mechanism by which a potentially injurious immune response is prevented, suppressed, or shifted to a non-injurious immune response (Bach, et al., N. Eng. J. Med., 347:911-920 (2002)).

As used herein, the term "tolerizing vaccine" as used herein is typically an antigen-specific therapy used to attenuate autoreactive T and/or B cell responses, while leaving global immune function intact.

As used herein, the term "immunogenic agent" or "immunogen" or "antigen" is capable of inducing an immunological response against itself on administration to a mammal, optionally in conjunction with an adjuvant.

As used herein, the term "carrier" refers to an organic or inorganic ingredient, natural or synthetic, with which the active ingredient is combined to facilitate the application.

As used herein, the term "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

As used herein, the term "pharmaceutically acceptable carrier" means one or more compatible solid or liquid fillers, diluents or encapsulating substances which are suitable for administration to a human or other vertebrate animal.

As used herein, the term "treating" includes inhibiting, alleviating, preventing or eliminating one or more symptoms or side effects associated with a disease or disorder.

As used herein, the term "reduce", "inhibit", "alleviate" or "decrease" are used relative to a control. One of skill in the art would readily identify the appropriate control to use for each experiment.

As used herein, the terms "subject," "individual," and "patient" refer to any individual who is the target of treatment using the disclosed compositions. The subject can be a vertebrate, for example, a mammal. Thus, the subject can be a human. The subjects can be symptomatic or asymptomatic. The term does not denote a particular age or sex. Thus, adult and newborn subjects, whether male or female, are intended to be covered. A subject can include a control subject or a test subject.

II. Nanocage Particles

Cage-like nanoparticles composed of saponin, sterol, lipid, and additional adjuvant (e.g., TLR4 agonist) (also referred to as "nanocages") are provided. A plurality of the nanocages can be used as an adjuvant. In some embodiments, the nanocages further include one or more antigens. In some embodiments, the nanocages do not include or incorporate antigen, but nanocage particles are present in a pharmaceutical composition with antigen (e.g., free antigen). In some embodiments, the nanocage adjuvant and antigen are part of two separate compositions. Exemplary saponins, sterols, lipids, additional adjuvants including TLR4 agonists, and antigens are discussed in more detail below.

Generally, the nanocage adjuvant is formed by mixing the components together in the presence of a detergent in a suitable ratio such that when the detergent is removed (e.g., by dialysis), the components self-assemble into nanocages. The size of the nanocages is typically dictated by the properties of the components and the self-assembly process. The disclosed compositions and methods typically yield nanocages in the range of about 30 nm and about 60 nm, or about 40 nm to about 50 nm, with a preferred size being about 40 nm.

The nanocages generally assume a distinctive porous morphology that can be structurally distinguished by transmission electronic microscope (TEM) from lipid monolayer (micelle) and lipid bilayer (liposome) particles. For example, in some embodiments, the morphological structure of the nanocages is the same or similar to the morphological structure of ISCOMATRIX®, as described and imaged in Morelli and Maraskovsky, Chapter 16—ISCOMATRIX Adjuvant in the Development of Prophylactic and Therapeutic Vaccines, Immunopotentiators in Modern Vaccines (Second Edition) 2017, Pages 311-332. Thus, preferably, the particles are not micelles or liposomes.

A. Saponin

The nanocages typically include one or more saponins. A suitable saponin is one that can induce or enhance an immune response. Saponins from plants have proven to be very effective as adjuvants. Saponins are triterpene and steroid glycosides widely distributed in the plant kingdom. Structurally, saponins are amphiphilic surfactants, which explains their surfactant properties, ability to form colloidal solutions, hemolytic activity and ability to form mixed micelles with lipids and sterols. The saponins most studied and used as adjuvants are those from Chilean tree Quillaja saponaria, which have cellular and humoral adjuvant activity. Saponins extracts from Quillaja saponaria with adjuvant activity are known and employed in commercial or experimental vaccines formulation.

A particular saponin preparation is called Quil A. Quil A is a saponin preparation isolated from the South American tree Ouillaja Saponaria Molina and was first described by Dalsgaard et al. in 1974 ("Saponin adjuvants," Archiv. für die gesamte Virus forschung, Vol. 44, Springer Verlag, Berlin, p 243-254) to have adjuvant activity. The isolation of pure saponins or better defined mixtures from the Quil A product having adjuvant activity and lower toxicity than Quil A have also been described. Purified fragments of Quil A that retain adjuvant activity without the toxicity associated with Quil A (EP 0362 278), for example QS7 and QS21 (also known as QA7 and QA21), have been isolated by HPLC. QS-21 is a natural saponin derived from the bark of Quillaja Saponaria Molina, which induces CD8+cytotoxic T cells (CTLs), Th1 cells and a predominant IgG2a antibody response. QS-21 has been used or is being studied as an adjuvant for various types of vaccines. See also EP 0 362 279 B1 and U.S. Pat. No. 5,057,540.

The isolation and adjuvant activity of other isolated Quil A saponins, including those called QS-17, and 18 have also been reported, and can also be used in the disclosed nanocages In other embodiments, the saponin is from Quillaja brasiliensis (A. St.-Hil. et Tul.) Mart., which is native to southern Brazil and Uruguay and has saponins that have proven to be effective as adjuvants with a similar activity against viral antigens as Quil A (Silveira et al., Vaccine 29 (2011), 9177-9182).

Other useful saponins are derived from the plants Aesculus hippocastanum or Gyophila Struthium. Other saponins which have been described in the literature include escin, which has been described in the Merck index (12th ed: entry 3737) as a mixture of saponins occurring in the seed of the horse chestnut tree, Lat: Aesculus hippocastanum. Its isolation by chromatography and purification (Fiedler, Arzneimittel-Forsch. 4, 213 (1953)), and by ion exchange resins (Erbring et al., U.S. Pat. No. 3,238,190) has been described. Fractions of escin have been purified and shown to be biologically active (Yoshikawa M, et al. (Chem Pharm Bull (Tokyo) August 1996; 44(8): 1454-1464)). Sapoalbin from Gypsophila struthium (R. Vochten et al., 1968, J. Pharm. Belg., 42, 213-226) has also been described.

In other embodiments, the saponin is a synthetic saponin. See, e.g., U.S. Published Application No. 2011/0300177 and U.S. Pat. No. 8,283,456, which describe the Triterpene Saponin Synthesis Technology (TriSST) platform, a convergent synthetic approach in which the four domains in QS-21 (branched trisaccharide+triterpene+linear tetrasaccharide+ fatty acyl chain) are synthesized separately and then assembled to produce the target molecule. Each of the domains can be modified independently and then combined to produce a virtually infinite number of rationally designed QS-21 analogs. Initially, fully synthetic QS-21(SQS-21) was shown to be safe and immunologically active in a Phase 1 clinical trial, and later over 100 analogues were prepared and tested in a systematic sequential series of studies. See, e.g., Ragupathi, et al., Expert Rev Vaccines. 2011 April; 10(4): 463-470. See also Zu, et al., Journal of Carbohydrate Chemistry, Volume 33, 2014—Issue 6, pages 269-97.

Preferably the saponin component is in a substantially pure form, for example, at least 90% pure, preferably at least 95% pure and most preferably at least 98% pure.

B. Sterol

The nanocages typically include one or more sterols. Sterols include (3-sitosterol, stigmasterol, ergosterol, ergocalciferol, campesterol, and cholesterol. These sterols are well known in the art, for example cholesterol is disclosed in the Merck Index, 11th Ed., page 341, as a naturally occurring sterol found in animal fat. In preferred embodiments, the sterol is cholesterol or a derivative thereof e.g., ergosterol or cholesterylhemisuccinate.

C. Lipid

The nanocages typically include one or more lipids, preferably one or more phospholipids. The lipid can be neutral, anionic, or cationic at physiologic pH. Phospholipids include, but are not limited to, diacylglycerides such as phosphatidic acid (phosphatidate) (PA), phosphatidylethanolamine (cephalin) (PE), phosphatidylcholine (lecithin) (PC), phosphatidylserine (PS), and phosphoinositides, e.g., phosphatidylinositol (PI), phosphatidylinositol phosphate (PIP), phosphatidylinositol bisphosphate (PIP2) and phosphatidylinositol trisphosphate (PIP3), as well as phosphoshingolipids such as ceramide phosphorylcholine (Sphingomyelin) (SPH), ceramide phosphorylethanolamine (Sphingomyelin) (Cer-PE), and ceramide phosphoryllipid, and natural and synthetic phospholipid derivatives such as egg PC (Egg lecithin), egg PG, soy PC, hydrogenated soy PC, sphingomyelin, phosphatidic acid (DMPA, DPPA, DSPA), phosphatidylcholine (DDPC, DLPC, DMPC, DPPC, DSPC, DOPC, POPC, DEPC), phosphatidylglycerol (DMPG, DPPG, DSPG, POPG), phosphatidylethanolamine (DMPE, DPPE, DSPE DOPE), phosphatidylserine (DOPS), and PEG phospholipid (mPEG-phospholipid, polyglycerin-phospholipid, functionalized-phospholipid, terminal activated-phospholipid).

Thus, nanocage can include any one of more of 1,2-Didecanoyl-sn-glycero-3-phosphocholine (DDPC), 1,2-Dierucoyl-sn-glycero-3-phosphate (Sodium Salt) (DEPA-NA), 1,2-Dierucoyl-sn-glycero-3-phosphocholine (DEPC), 1,2-Dierucoyl-sn-glycero-3-phosphoethanolamine (DEPE) 1,2-Dierucoyl-sn-glycero-3[Phospho-rac-(1-glycerol) (Sodium Salt) (DEPG-NA), 1,2-Dilinoleoyl-sn-glycero-3-phosphocholine (DLOPC), 1,2-Dilauroyl-sn-glycero-3-phosphate (Sodium Salt) (DLPA-NA) 1,2-Dilauroyl-sn-glycero-3-phosphocholine (DLPC) 1,2-Dilauroyl-sn-glycero-3-phosphoethanolamine (DLPE), 1,2-Dilauroyl-sn-glycero-3 [Phospho-rac-(1-glycerol) (Sodium Salt) (DLPG-NA), 1,2-Dilauroyl-sn-glycero-3[Phospho-rac-(1-glycerol) (Ammonium Salt) (DLPG-NH4), 1,2-Dilauroyl-sn-glycero-3-phosphoserine (Sodium Salt) (DLPS-NA), 1,2-Dimyristoyl-sn-glycero-3-phosphate (Sodium Salt) (DMPA-NA), 1,2-Dimyristoyl-sn-glycero-3-phosphocholine (DMPC), 1,2-Dimyristoyl-sn-glycero-3-phosphoethanolamine (DMPE), 1,2-Dimyristoyl-sn-glycero-3[Phospho-rac-(1-glycerol) (Sodium Salt) (DMPG-NA), 1,2-Dimyristoyl-sn-glycero-3[Phospho-rac-(1-glycerol) (Ammonium Salt) (DMPG-NH4), 1,2-Dimyristoyl-sn-glycero-3[Phospho-rac-(1-glycerol) (Sodium/Ammonium Salt) (DMPG-NH4/NA), 1,2-Dimyristoyl-sn-glycero-3-phosphoserine (Sodium Salt) (DMPS-NA), 1,2-Dioleoyl-sn-glycero-3-phosphate (Sodium Salt) (DOPA-NA), 1,2-Dioleoyl-sn-glycero-3-phosphocholine (DOPC), 1,2-Dioleoyl-sn-glycero-3-phosphoethanolamine (DOPE), 1,2-Dioleoyl-sn-glycero-3[Phospho-rac-(1-glycerol) (Sodium Salt) (DOPG-NA), 1,2-Dioleoyl-sn-glycero-3-phosphoserine (Sodium Salt) (DOPS-NA), 1,2-Dipalmitoyl-sn-glycero-3-phosphate (Sodium Salt) (DPPA-NA), 1,2-Dipalmitoyl-sn-glycero-3-phosphocholine (DPPC), 1,2-Dipalmitoyl-sn-glycero-3-phosphoethanolamine (DPPE), 1,2-Dipalmitoyl-sn-glycero-3[Phospho-rac-(1-glycerol) (Sodium Salt) (DPPG-NA), 1,2-Dipalmitoyl-sn-glycero-3[Phospho-rac-(1-glycerol) (Ammonium Salt) (DPPG-NH4), 1,2-Dipalmitoyl-sn-glycero-3-phosphoserine (Sodium Salt) (DPPS-NA), 1,2-Distearoyl-sn-glycero-3-phosphate (Sodium Salt) (DSPA-NA), 1,2-Distearoyl-sn-glycero-3-phosphocholine (DSPC), 1,2-Distearoyl-sn-glycero-3-phosphoethanolamine (DSPE), 1,2-Distearoyl-sn-glycero-3[Phospho-rac-(1-glycerol) (Sodium Salt) (DSPG-NA), 1,2-Distearoyl-sn-glycero-3[Phospho-rac-(1-glycerol) (Ammonium Salt) (DSPG-NH4), 1,2-Distearoyl-sn-glycero-3-phosphoserine (Sodium Salt) (DSPS-NA), Egg-PC (EPC), Hydrogenated Egg PC (HEPC), Hydrogenated Soy PC (HSPC), 1-Myristoyl-sn-glycero-3-phosphocholine (LYSOPC MYRISTIC), 1-Palmitoyl-sn-glycero-3-phosphocholine (LYSOPC PALMITIC), 1-Stearoyl-sn-glycero-3-phosphocholine (LYSOPC STEARIC), 1-Myristoyl-2-palmitoyl-sn-glycero 3-phosphocholine (Milk Sphingomyelin MPPC), 1-Myristoyl-2-stearoyl-sn-glycero-3-phosphocholine (MSPC), 1-Palmitoyl-2-myristoyl-sn-glycero-3-phosphocholine (PMPC), 1-Palmitoyl-2-oleoyl-sn-glycero-3-phosphocholine (POPC), 1-Palmitoyl-2-oleoyl-sn-glycero-3-phosphoethanolamine (POPE), 1-Palmitoyl-2-oleoyl-sn-glycero-3[Phospho-rac-(1-glycerol) . . . ] (Sodium Salt) (POPG-NA), 1-Palmitoyl-2-stearoyl-sn-glycero-3-phosphocholine (PSPC), 1-Stearoyl-2-myristoyl-sn-glycero-3-phosphocholine (SMPC), 1-Stearoyl-2-oleoyl-sn-glycero-3-phosphocholine (SOPC), and 1-Stearoyl-2-palmitoyl-sn-glycero-3-phosphocholine (SPPC). Any of the lipids can be PEGylated lipids, for example PEG-DSPE.

D. Adjuvant

The nanocages typically include one or more adjuvants in addition to a saponin. The additional adjuvant typically has physical and biochemical properties compatible with its incorporation into structure of the nanocage and that do not prevented nanocage self-assembly. The additional adjuvant also typically increases at least one immune response relative to the same nanocage formulation in the absence of the additional adjuvant. Immune responses include, but are not limited to, an increase in an antigen-specific antibody response (e.g., IgG, IgG2a, IgG1, or a combination thereof), an increase in a response in germinal centers (e.g., increase in the frequency of germinal center B cells, an increase in frequencies and/or activation of T follicular helper (Tfh) cells, an increase in B cell presence or residence in dark zone of germinal center or a combination thereof), an increase in plasmablast frequency, an increase in inflammatory cytokine expression (e.g., IL-6, IFN-7, IFN-α, IL-1β, TNF-α, CXCL10 (IP-10), or a combination thereof), an increase in drainage of antigen from the injection site, an in increase in antigen accumulation in the lymph nodes, an increase in lymph node permeability, an increase in lymph flow, an increase in antigen-specific B cell antigen uptake in lymph nodes, an increase in humoral responses beyond the proximal lymph node, increased diffusion of antigen into B cell follicles, or a combination thereof, when the nanocages are administered to a subject, preferably in combination with an antigen.

1. TLR4 Agonists

In preferred embodiments, the additional adjuvant is a TLR agonist. TLR4 is a transmembrane protein member of the toll-like receptor family, which belongs to the pattern recognition receptor (PRR) family. Its activation leads to an intracellular signaling pathway NF-κB and inflammatory cytokine production responsible for activating the innate immune system. Classes of TLR agonists include, but are not limited to, viral proteins, polysaccharides, and a variety of endogenous proteins such as low-density lipoprotein, beta-defensins, and heat shock protein.

Exemplary TLR4 agonist include without limitation derivatives of lipopolysaccharides such as monophosphoryl lipid A (MPLA; Ribi ImmunoChem Research, Inc., Hamilton, Mont.) and muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland).

In a preferred embodiment, the TLR4 agonist is a natural or synthetic lipopolysaccharide (LPS), or a lipid A derivative thereof such as MPLA or 3D-MPLA. Lipopolysaccharides are the major surface molecule of, and occur exclusively in, the external leaflet of the outer membrane of gram-negative bacteria. LPS impede destruction of bacteria by serum complements and phagocytic cells, and are involved in adherence for colonization. LPS are a group of structurally related complex molecules of approximately 10,000 Daltons in size and contain three covalently linked regions: (i) an O-specific polysaccharide chain (0-antigen) at the outer region (ii) a core oligosaccharide central region (iii) lipid A—the innermost region which serves as the hydrophobic anchor, it includes glucosamine disaccharide units which carry long chain fatty acids.

The biological activities of LPS, such as lethal toxicity, pyrogenicity and adjuvanticity, have been shown to be related to the lipid A moiety. In contrast, immunogenicity is associated with the O-specific polysaccharide component (0-antigen). Both LPS and lipid A have long been known for their strong adjuvant effects, but the high toxicity of these molecules has precluded their use in vaccine formulations. Significant effort has therefore been made towards reducing the toxicity of LPS or lipid A while maintaining their adjuvanticity.

The *Salmonella minnesota* mutant R595 was isolated in 1966 from a culture of the parent (smooth) strain (Luderitz et al. 1966 Ann. N. Y. Acad. Sci. 133:349-374). The colonies selected were screened for their susceptibility to lysis by a panel of phages, and only those colonies that displayed a narrow range of sensitivity (susceptible to one or two phages only) were selected for further study. This effort led to the isolation of a deep rough mutant strain which is defective in LPS biosynthesis and referred to as *S. minnesota* R595.

In comparison to other LPS, those produced by the mutant *S. minnesota* R595 have a relatively simple structure. (i) they contain no O-specific region—a characteristic which is responsible for the shift from the wild type smooth phenotype to the mutant rough phenotype and results in a loss of virulence (ii) the core region is very short—this characteristic increases the strain susceptibility to a variety of chemicals (iii) the lipid A moiety is highly acylated with up to 7 fatty acids.

4'-monophosporyl lipid A (MPLA), which may be obtained by the acid hydrolysis of LPS extracted from a deep rough mutant strain of gram-negative bacteria, retains the adjuvant properties of LPS while demonstrating a toxicity which is reduced by a factor of more than 1000 (as measured by lethal dose in chick embryo eggs) (Johnson et al. 1987 Rev. Infect. Dis. 9 Suppl:S512-S516). LPS is typically refluxed in mineral acid solutions of moderate strength (e.g. 0.1 M HCl) for a period of approximately 30 minutes. This process results in dephosphorylation at the 1 position, and decarbohydration at the 6' position, yielding MPLA. In some embodiments, the TLR4 agonist is MPLA.

3-O-deacylated monophosphoryl lipid A (3D-MPLA), which can be obtained by mild alkaline hydrolysis of MPLA, has a further reduced toxicity while again maintaining adjuvanticity, see U.S. Pat. No. 4,912,094 (Ribi Immunochemicals). Alkaline hydrolysis is typically performed in organic solvent, such as a mixture of chloroform/methanol, by saturation with an aqueous solution of weak base, such as 0.5 M sodium carbonate at pH 10.5. In some embodiments, the TLR4 agonist is 3D-MPLA.

In some embodiments, the MPLA is a fully synthetic MPLA such as Phosphorylated HexaAcyl Disaccharide (PHAD®), the first fully synthetic monophosphoryl Lipid A available for use as an adjuvant in human vaccines, or Monophosphoryl 3-Deacyl Lipid A (Synthetic) (3D-PHAD®). See also U.S. Pat. No. 9,241,988.

2. Other Exemplary Adjuvants

As introduced above, the additional adjuvant typically has physical and biochemical properties compatible with its incorporation into the structure of the nanocage and that do not prevented nanocage self-assembly and increase an immune response. Thus, other suitable adjuvants immunostimulators include those that include a lipid tail, or can be modified to contain a lipid tail. Examples of molecules that include a lipid tail, or can be modified to include one, can be, for example, pathogen-associated molecular patterns (PAMPs). PAMPS are recognized by pattern recognition receptors (PRRs). Five families of PRRs have been shown to initiate pro-inflammatory signaling pathways: Toll-like receptors (TLRs), NOD-like receptors (NLRs), RIG-I-like receptors (RLRs), C-type lectin receptors (CLRs) and cytosolic dsDNA sensors (CDSs). Also, some NLRs are involved in the formation of pro-inflammatory complexes called inflammasomes.

Thus, in some embodiments, the adjuvant is a TLR ligand, a NOD ligand, an RLR ligand, a CLR ligand, and inflammasome inducer, a STING ligand, or a combination thereof. Such ligands are known in the art can obtained through commercial vendors such as InvivoGen.

As introduced above, the ligands and other adjuvants can be modified (e.g., through chemical conjugation, for example, maleimide thiol reaction, amine N-hydroxysuccinimide ester reaction, click chemistry, etc.) to include a lipid tail to facilitate incorporation of the adjuvant into the nanocage structure during self-assembly. Preferred lipids will include a 16:0 dipalmitoyl tail such as 1,2-dipalmitoyl-sn-glycero-3-phosphoethanolamine-N-[4-(p-maleimidophenyl)butyramide], these, however, are non-limiting examples. For example, lipids of different lengths are also contemplated. In preferred embodiments, the lipid or lipids is/are unsaturated. Chemically functionalized lipids that that can be used for conjugation are known in the art and commercially available. See, for example, AVANTI® Polar Lipids, Inc. (e.g., "Headgroup Modified Lipids" and "Functionalized Lipids").

The adjuvant can be an immunostimulatory oligonucleotide, preferable a lipidated immunostimulatory oligonucleotide. Exemplary lapidated immunostimulatory oligonucleotides and methods of making them are described in Liu, et al., *Nature Letters*, 507:519-22 (+11 pages of extended data) (2014)) (lipo-CpG) and U.S. Pat. No. 9,107,904, that contents of which are incorporated by reference herein in their entireties. In some embodiments, the immunostimulatory oligonucleotide portion of the adjuvant can serve as a ligand for PRRs. Therefore, the oligonucleotide can serve as a ligand for a Toll-like family signaling molecule, such as Toll-Like Receptor 9 (TLR9).

For example, unmethylated CpG sites can be detected by TLR9 on plasmacytoid dendritic cells and B cells in humans (Zaida, et al., *Infection and Immunity*, 76(5):2123-2129, (2008)). Therefore, the sequence of the oligonucleotide can include one or more unmethylated cytosine-guanine (CG or CpG, used interchangeably) dinucleotide motifs. The 'p' refers to the phosphodiester backbone of DNA, as discussed in more detail below, some oligonucleotides including CG can have a modified backbone, for example a phosphorothioate (PS) backbone.

In some embodiments, an immunostimulatory oligonucleotide can contain more than one CG dinucleotide, arranged either contiguously or separated by intervening nucleotide(s). The CpG motif(s) can be in the interior of the oligonucleotide sequence. Numerous nucleotide sequences stimulate TLR9 with variations in the number and location of CG dinucleotide(s), as well as the precise base sequences flanking the CG dimers.

Typically, CG ODNs are classified based on their sequence, secondary structures, and effect on human peripheral blood mononuclear cells (PBMCs). The five classes are Class A (Type D), Class B (Type K), Class C, Class P, and Class S (Vollmer, J & Krieg, A M, Advanced drug delivery reviews 61(3): 195-204 (2009), incorporated herein by reference). CG ODNs can stimulate the production of Type I interferons (e.g., IFNα) and induce the maturation of dendritic cells (DCs). Some classes of ODNs are also strong activators of natural killer (NK) cells through indirect cytokine signaling. Some classes are strong stimulators of human B cell and monocyte maturation (Weiner, G L, *PNAS USA* 94(20): 10833-7 (1997); Dalpke, A H, *Immunology* 106(1): 102-12 (2002); Hartmann, G, *J of Immun.* 164(3): 1617-2 (2000), each of which is incorporated herein by reference).

Other PRR Toll-like receptors include TLR3, and TLR7 which may recognize double-stranded RNA, single-stranded and short double-stranded RNAs, respectively, and retinoic acid-inducible gene I (RIG-I)-like receptors, namely RIG-I and melanoma differentiation-associated gene 5 (MDA5), which are best known as RNA-sensing receptors in the cytosol. Therefore, in some embodiments, the oligonucleotide contains a functional ligand for TLR3, TLR7, or RIG-I-like receptors, or combinations thereof.

Examples of immunostimulatory oligonucleotides, and methods of making them are known in the art, see for example, Bodera, P. Recent Pat Inflamm Allergy Drug Discov. 5(1):87-93 (2011), incorporated herein by reference.

In some embodiments, the oligonucleotide includes two or more immunostimulatory sequences.

Microbial cell-wall components such as Pam2CSK4, Pam3CSK4, and flagellin activate TLR2 and TLR5 receptors respectively and can also be used.

E. Antigen

As discussed herein, antigen refers to the molecule to which an immune response is desired. The antigen can be a component of the nanocage structure itself and/or separate and distinct therefrom (e.g., distinct from the saponin, sterol, lipid, and additional adjuvant (e.g., TLR4 agonist) components). Thus, in some embodiments, the nanocages can optionally include, encapsulate, or incorporate one or more antigens. Such nanocages can thus serve as both adjuvant and antigen in an immunogenic or vaccine formulation. In other embodiments, the nanocages are formed of saponin, sterol, lipid, and additional adjuvant (e.g., additional adjuvant (e.g., TLR4 agonist)) components and absent or free of an antigen. In such embodiments, the nanocages typically serve as an adjuvant only. In some such embodiments, antigen (e.g., free antigen) is present in a pharmaceutical composition in combination with a nanocage adjuvant that is free from/of the antigen.

Antigens can be peptides, proteins, polysaccharides, saccharides, lipids, nucleic acids, or combinations thereof. The antigen can be derived from a virus, bacterium, parasite, plant, protozoan, fungus, tissue or transformed cell such as a cancer or leukemic cell and can be a whole cell or immunogenic component thereof, e.g., cell wall components or molecular components thereof.

Suitable antigens are known in the art and are available from commercial, government, and scientific sources. The antigens are whole inactivated or attenuated organisms, or derived therefrom. These organisms may be infectious organisms, such as viruses, parasites and bacteria. These organisms may also be tumor cells, or derived therefrom. For example, the antigens may be purified or partially purified polypeptides derived from tumors or viral or bacterial sources. The antigens can be recombinant polypeptides produced by expressing DNA encoding the polypeptide antigen in a heterologous expression system. The antigens can be DNA encoding all or part of an antigenic protein. The DNA may be in the form of vector DNA such as plasmid DNA.

Antigens may be provided as single antigens or may be provided in combination. Antigens may also be provided as complex mixtures of polypeptides or nucleic acids. Exemplary antigens are provided below.

1. Viral antigens

A viral antigen can be isolated from any virus including, but not limited to, a virus from any of the following viral families: Arenaviridae, Arterivirus, Astroviridae, Baculoviridae, Badnavirus, Barnaviridae, Birnaviridae, Bromoviridae, Bunyaviridae, Caliciviridae, Capillovirus, Carlavirus, Caulimovirus, Circoviridae, Closterovirus, Comoviridae, Coronaviridae (e.g., Coronavirus, such as severe acute respiratory syndrome (SARS) virus), Corticoviridae, Cystoviridae, Deltavirus, Dianthovirus, Enamovirus, Filoviridae (e.g., Marburg virus and Ebola virus (e.g., Zaire, Reston, Ivory Coast, or Sudan strain)), Flaviviridae, (e.g., Hepatitis C virus, Dengue virus 1, Dengue virus 2, Dengue virus 3, and Dengue virus 4), Hepadnaviridae, Herpesviridae (e.g., Human herpesvirus 1, 3, 4, 5, and 6, and Cytomegalovirus), Hypoviridae, Iridoviridae, Leviviridae, Lipothrixviridae, Microviridae, Orthomyxoviridae (e.g., Influenzavirus A and B and C), Papovaviridae, Paramyxoviridae (e.g., measles, mumps, and human respiratory syncytial virus), Parvoviridae, Picornaviridae (e.g., poliovirus, rhinovirus, hepatovirus, and aphthovirus), Poxviridae (e.g., vaccinia and smallpox virus), Reoviridae (e.g., rotavirus), Retroviridae (e.g., lentivirus, such as human immunodeficiency virus (HIV) 1 and HIV 2), Rhabdoviridae (for example, rabies virus, measles virus, respiratory syncytial virus, etc.), Togaviridae (for example, rubella virus, dengue virus, etc.), and Totiviridae. Suitable viral antigens also include all or part of Dengue protein M, Dengue protein E, Dengue D1NS1, Dengue D1NS2, and Dengue D1NS3.

Viral antigens may be derived from a particular strain such as a papilloma virus, a herpes virus, e.g., herpes simplex 1 and 2; a hepatitis virus, for example, hepatitis A virus (HAV), hepatitis B virus (HBV), hepatitis C virus (HCV), the delta hepatitis D virus (HDV), hepatitis E virus (HEV) and hepatitis G virus (HGV), the tick-borne encephalitis viruses; parainfluenza, varicella-zoster, cytomeglavirus, Epstein-Barr, rotavirus, rhinovirus, adenovirus, coxsackieviruses, equine encephalitis, Japanese encephalitis, yellow fever, Rift Valley fever, and lymphocytic choriomeningitis.

2. Bacterial Antigens

Bacterial antigens can originate from any bacteria including, but not limited to, *Actinomyces, Anabaena, Bacillus, Bacteroides, Bdellovibrio, Bordetella, Borrelia, Campylobacter, Caulobacter, Chlamydia, Chlorobium, Chromatium, Clostridium, Corynebacterium, Cytophaga, Deinococcus, Escherichia, Francisella, Halobacterium, Heliobacter, Haemophilus*, Hemophilus influenza type B (HIB), *Hyphomicrobium, Legionella, Leptspirosis, Listeria*, Meningococcus A, B and C, *Methanobacterium, Micrococcus, Myobacterium, Mycoplasma, Myxococcus, Neisseria, Nitrobacter, Oscillatoria*, Prochloron, *Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus*, and *Treponema, Vibrio*, and *Yersinia*.

3. Parasite Antigens

Parasite antigens can be obtained from parasites such as, but not limited to, an antigen derived from *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psit-* taci, *Chlamydial trachomatis, Plasmodium falciparum, Trypanosoma brucei, Entamoeba histolytica, Toxoplasma gondii, Trichomonas vaginalis* and *Schistosoma mansoni*. These include Sporozoan antigens, Plasmodian antigens, such as all or part of a Circumsporozoite protein, a Sporozoite surface protein, a liver stage antigen, an apical membrane associated protein, or a Merozoite surface protein.

4. Allergens and Environmental Antigens

The antigen can be an allergen or environmental antigen, such as, but not limited to, an antigen derived from naturally occurring allergens such as pollen allergens (tree-, herb, weed-, and grass pollen allergens), insect allergens (inhalant, saliva and venom allergens), animal hair and dandruff allergens, and food allergens. Important pollen allergens from trees, grasses and herbs originate from the taxonomic orders of Fagales, Oleales, Pinales and platanaceae including i.a. birch (*Betula*), alder (*Alnus*), hazel (*Corylus*), hornbeam (*Carpinus*) and olive (*Olea*), cedar (Cryptomeriaand *Juniperus*), Plane tree (*Platanus*), the order of Poales including e.g., grasses of the genera *Lolium, Phleum, Poa, Cynodon, Dactylis, Holcus, Phalaris, Secale*, and Sorghum, the orders of Asterales and Urticales including i.a. herbs of the genera *Ambrosia, Artemisia*, and *Parietaria*. Other allergen antigens that may be used include allergens from house dust mites of the genus *Dermatophagoides* and Euroglyphus, storage mite e.g. Lepidoglyphys, Glycyphagus and Tyrophagus, those from cockroaches, midges and fleas e.g. Blatella, *Periplaneta*, Chironomus and Ctenocepphalides, those from mammals such as cat, dog and horse, birds, venom allergens including such originating from stinging or biting insects such as those from the taxonomic order of Hymenoptera including bees (superfamily Apidae), wasps (superfamily Vespidea), and ants (superfamily Formicoidae). Still other allergen antigens that may be used include inhalation allergens from fungi such as from the genera *Alternaria* and *Cladosporium*.

5. Cancer Antigens

A cancer antigen is an antigen that is typically expressed preferentially by cancer cells (i.e., it is expressed at higher levels in cancer cells than on non-cancer cells) and in some instances it is expressed solely by cancer cells. The cancer antigen may be expressed within a cancer cell or on the surface of the cancer cell. The cancer antigen can be MART-1/Melan-A, gp100, adenosine deaminase-binding protein (ADAbp), FAP, cyclophilin b, colorectal associated antigen (CRC)—C017-1A/GA733, carcinoembryonic antigen (CEA), CAP-1, CAP-2, etv6, AML1, prostate specific antigen (PSA), PSA-1, PSA-2, PSA-3, prostate-specific membrane antigen (PSMA), T cell receptor/CD3-zeta chain, and CD20. The cancer antigen may be selected from the group consisting of MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-Xp2 (MAGE-B2), MAGE-Xp3 (MAGE-B3), MAGE-Xp4 (MAGE-B4), MAGE-C1, MAGE-C2, MAGE-C3, MAGE-C4, MAGE-C5), GAGE-1, GAGE-2, GAGE-3, GAGE-4, GAGE-5, GAGE-6, GAGE-7, GAGE-8, GAGE-9, BAGE, RAGE, LAGE-1, NAG, GnT-V, MUM-1, CDK4, tyrosinase, p53, MUC family, HER2/neu, p21ras, RCAS1, α-fetoprotein, E-cadherin, α-catenin, β-catenin, γ-catenin, p120ctn, gp100Pmel117, PRAME, NY-ESO-1, cdc27, adenomatous polyposis *coli* protein (APC), fodrin, Connexin 37, Ig-idiotype, p15, gp75, GM2 ganglioside, GD2 ganglioside, human papilloma virus proteins, Smad family of tumor antigens, lmp-1, P1A, EBV-encoded nuclear antigen (EBNA)-1, brain glycogen phosphorylase, SSX-1, SSX-2 (HOM-MEL-40), SSX-1, SSX-4, SSX-5, SCP-1 and CT-7, CD20, or c-erbB-2.

6. Tolerogenic Antigens

The antigen can be a tolerogenic antigen. Exemplary antigens are known in the art. See, for example, U.S. Published Application No. 2014/0356384.

In some cases, the tolerogenic antigen is derived from a therapeutic agent protein to which tolerance is desired. Examples are protein drugs in their wild type, e.g., human factor VIII or factor IX, to which patients did not establish central tolerance because they were deficient in those proteins; or nonhuman protein drugs, used in a human. Other examples are protein drugs that are glycosylated in nonhuman forms due to production, or engineered protein drugs, e.g., having non-native sequences that can provoke an unwanted immune response. Examples of tolerogenic antigens that are engineered therapeutic proteins not naturally found in humans including human proteins with engineered mutations, e.g., mutations to improve pharmacological characteristics. Examples of tolerogenic antigens that have non-human glycosylation include proteins produced in yeast or insect cells.

Tolerogenic antigens can be from proteins that are administered to humans that are deficient in the protein. Deficient means that the patient receiving the protein does not naturally produce enough of the protein. Moreover, the proteins may be proteins for which a patient is genetically deficient. Such proteins include, for example, antithrombin-III, protein C, factor VIII, factor IX, growth hormone, somatotropin, insulin, pramlintide acetate, mecasermin (IGF-1), β-glucocerebrosidase, alglucosidase-.alpha., laronidase (α-L-iduronidase), idursuphase (iduronate-2-sulphatase), galsulphase, agalsidase-.beta. (α-galactosidase), α-1 proteinase inhibitor, and albumin.

The tolerogenic antigen can be from therapeutic antibodies and antibody-like molecules, including antibody fragments and fusion proteins with antibodies and antibody fragments. These include nonhuman (such as mouse) antibodies, chimeric antibodies, and humanized antibodies. Immune responses to even humanized antibodies have been observed in humans (Getts D R, Getts M T, McCarthy D P, Chastain E M L, & Miller S D (2010), mAbs, 2(6):682-694).

The tolerogenic antigen can be from proteins that are nonhuman. Examples of such proteins include adenosine deaminase, pancreatic lipase, pancreatic amylase, lactase, botulinum toxin type A, botulinum toxin type B, collagenase, hyaluronidase, papain, L-Asparaginase, rasburicase, lepirudin, streptokinase, anistreplase (anisoylated plasminogen streptokinase activator complex), antithymocyte globulin, crotalidae polyvalent immune Fab, digoxin immune serum Fab, L-arginase, and L-methionase.

Tolerogenic antigens include those from human allograft transplantation antigens. Examples of these antigens are the subunits of the various MHC class I and MHC class II haplotype proteins, and single-amino-acid polymorphisms on minor blood group antigens including RhCE, Kell, Kidd, Duffy and Ss.

The tolerogenic antigen can be a self-antigen against which a patient has developed an autoimmune response or may develop an autoimmune response. Examples are proinsulin (diabetes), collagens (rheumatoid arthritis), myelin basic protein (multiple sclerosis). For instance, Type 1 diabetes mellitus (T1D) is an autoimmune disease whereby T cells that recognize islet proteins have broken free of immune regulation and signal the immune system to destroy pancreatic tissue. Numerous protein antigens that are targets of such diabetogenic T cells have been discovered, including insulin, GAD65, chromogranin-A, among others. In the treatment or prevention of T1D, it would be useful to induce antigen-specific immune tolerance towards defined diabetogenic antigens to functionally inactivate or delete the diabetogenic T cell clones.

Tolerance and/or delay of onset or progression of autoimmune diseases may be achieved for various of the many proteins that are human autoimmune proteins, a term referring to various autoimmune diseases wherein the protein or proteins causing the disease are known or can be established by routine testing. In some embodiments, a patient is tested to identify an autoimmune protein and an antigen is created for use in a molecular fusion to create immunotolerance to the protein.

Embodiments can include an antigen, or choosing an antigen from or derived from, one or more of the following proteins. In type 1 diabetes mellitus, several main antigens have been identified: insulin, proinsulin, preproinsulin, glutamic acid decarboxylase-65 (GAD-65), GAD-67, insulinoma-associated protein 2 (IA-2), and insulinoma-associated protein 2.beta. (IA-213); other antigens include ICA69, ICA12 (SOX-13), carboxypeptidase H, Imogen 38, GLIMA 38, chromogranin-A, FISP-60, caboxypeptidase E, peripherin, glucose transporter 2, hepatocarcinoma-intestine-pancreas/pancreatic associated protein, S1000, glial fibrillary acidic protein, regenerating gene II, pancreatic duodenal homeobox 1, dystrophia myotonica kinase, islet-specific glucose-6-phosphatase catalytic subunit-related protein, and SST G-protein coupled receptors 1-5. In autoimmune diseases of the thyroid, including Hashimoto's thyroiditis and Graves' disease, main antigens include thyroglobulin (TG), thyroid peroxidase (TPO) and thyrotropin receptor (TSHR); other antigens include sodium iodine symporter (NIS) and megalin. In thyroid-associated ophthalmopathy and dermopathy, in addition to thyroid autoantigens including TSHR, an antigen is insulin-like growth factor 1 receptor. In hypoparathyroidism, a main antigen is calcium sensitive receptor. In Addison's disease, main antigens include 21-hydroxylase, 17α-hydroxylase, and P450 side chain cleavage enzyme (P450scc); other antigens include ACTH receptor, P450c21 and P450c17. In premature ovarian failure, main antigens include FSH receptor and .alpha.-enolase. In autoimmune hypophysitis, or pituitary autoimmune disease, main antigens include pituitary gland-specific protein factor (PGSF) 1a and 2; another antigen is type 2 iodothyronine deiodinase. In multiple sclerosis, main antigens include myelin basic protein, myelin oligodendrocyte glycoprotein and proteolipid protein. In rheumatoid arthritis, a main antigen is collagen II. In immunogastritis, a main antigen is H+, K+-ATPase. In pernicious angemis, a main antigen is intrinsic factor. In celiac disease, main antigens are tissue transglutaminase and gliadin. In vitiligo, a main antigen is tyrosinase, and tyrosinase related protein 1 and 2. In myasthenia gravis, a main antigen is acetylcholine receptor. In pemphigus vulgaris and variants, main antigens are desmoglein 3, 1 and 4; other antigens include pemphaxin, desmocollins, plakoglobin, perplakin, desmoplakins, and acetylcholine receptor. In bullous pemphigoid, main antigens include BP180 and BP230; other antigens include plectin and laminin 5. In dermatitis herpetiformis Duhring, main antigens include endomysium and tissue transglutaminase. In epidermolysis bullosa acquisita, a main antigen is collagen VII. In systemic sclerosis, main antigens include matrix metalloproteinase 1 and 3, the collagen-specific molecular chaperone heat-shock protein 47, fibrillin-1, and PDGF receptor; other antigens include Scl-70, U1 RNP, Th/To, Ku, Jo1, NAG-2, centromere proteins, topoisomerase I, nucleolar proteins, RNA polymerase I, II and III, PM-Slc, fibrillarin, and B23. In mixed connective tissue disease, a main antigen is U1snRNP. In Sjogren's syndrome, the main antigens are nuclear antigens SS-A and SS-B; other antigens include fodrin, poly(ADP-ribose) polymerase and topoisomerase. In systemic lupus erythematosus, main antigens include nuclear proteins including SS-A, high mobility group box 1 (HMGB1), nucleosomes, histone proteins and double-stranded DNA. In Goodpasture's syndrome, main antigens include glomerular basement membrane proteins including collagen IV. In rheumatic heart disease, a main antigen is cardiac myosin. Other autoantigens revealed in autoimmune polyglandular syndrome type 1 include aromatic L-amino acid decarboxylase, histidine decarboxylase, cysteine sulfinic acid decarboxylase, tryptophan hydroxylase, tyrosine hydroxylase, phenylalanine hydroxylase, hepatic P450 cytochromes P4501A2 and 2A6, SOX-9, SOX-10, calcium-sensing receptor protein, and the type 1 interferons interferon alpha, beta and omega.

In some cases, the tolerogenic antigen is a foreign antigen against which a patient has developed an unwanted immune response. Examples are food antigens. Some embodiments include testing a patient to identify foreign antigen and creating a molecular fusion that comprises the antigen and treating the patient to develop immunotolerance to the antigen or food. Examples of such foods and/or antigens are provided. Examples are from peanut: conarachin (Ara h 1), allergen II (Ara h 2), *arachis* agglutinin, conglutin (Ara h 6); from apple: 31 kda major allergen/disease resistance protein homolog (Mal d 2), lipid transfer protein precursor (Mal d 3), major allergen Mal d 1.03D (Mal d 1); from milk: .alpha.-lactalbumin (ALA), lactotransferrin; from kiwi: actinidin (Act c 1, Act d 1), phytocystatin, thaumatin-like protein (Act d 2), kiwellin (Act d 5); from mustard: 2S albumin (Sin a 1), 11 S globulin (Sin a 2), lipid transfer protein (Sin a 3), profilin (Sin a 4); from celery: profilin (Api g 4), high molecular weight glycoprotein (Api g 5); from shrimp: Pen a 1 allergen (Pen a 1), allergen Pen m 2 (Pen in 2), tropomyosin fast isoform; from wheat and/or other cereals: high molecular weight glutenin, low molecular weight glutenin, alpha- and gamma-gliadin, hordein, secalin, avenin; from strawberry: major strawberry allergy Fra a 1-E (Fra a 1), from banana: profilin (Mus xp 1).

Many protein drugs that are used in human and veterinary medicine induce immune responses, which create risks for the patient and limits the efficacy of the drug. This can occur with human proteins that have been engineered, with human proteins used in patients with congenital deficiencies in production of that protein, and with nonhuman proteins. It would be advantageous to tolerize a recipient to these protein drugs prior to initial administration, and it would be advantageous to tolerize a recipient to these protein drugs after initial administration and development of immune response. In patients with autoimmunity, the self-antigen(s) to which autoimmunity is developed are known. In these cases, it would be advantageous to tolerize subjects at risk prior to development of autoimmunity, and it would be advantageous to tolerize subjects at the time of or after development of biomolecular indicators of incipient autoimmunity. For example, in Type 1 diabetes mellitus, immunological indicators of autoimmunity are present before broad destruction of beta cells in the pancreas and onset of clinical disease involved in glucose homeostasis. It would be advantageous to tolerize a subject after detection of these immunological indicators prior to onset of clinical disease.

7. Neoantigens and Personalized Medicine

In some embodiments the antigen is a neoantigen or a patient-specific antigen. Recent technological improvements have made it possible to identify the immune response to patient-specific neoantigens that arise as a consequence of tumor-specific mutations, and emerging data indicate that recognition of such neoantigens is a major factor in the activity of clinical immunotherapies (Schumacher and Schreidber, *Science*, 348(6230):69-74 (2015). Neoantigen load provides an avenue to selectively enhance T cell reactivity against this class of antigens.

Traditionally, cancer vaccines have targeted tumor-associated antigens (TAAs) which can be expressed not only on tumor cells but in the normal tissues (Ito, et al., Cancer Neoantigens: A Promising Source of Immunogens for Cancer Immunotherapy. *J Clin Cell Immunol*, 6:322 (2015) doi:10.4172/2155-9899.1000322). TAAs include cancer-testis antigens and differentiation antigens, and even though self-antigens have the benefit of being useful for diverse patients, expanded T cells with the high-affinity TCR (T-cell receptor) needed to overcome the central and peripheral tolerance of the host, which would impair anti-tumor T-cell activities and increase risks of autoimmune reactions.

Thus, in some embodiments, the antigen is recognized as "non-self" by the host immune system, and preferably can bypass central tolerance in the thymus. Examples include pathogen-associated antigens, mutated growth factor receptor, mutated K-ras, or idiotype-derived antigens. Somatic mutations in tumor genes, which usually accumulate tens to hundreds of fold during neoplastic transformation, could occur in protein-coding regions. Whether missense or frameshift, every mutation has the potential to generate tumor-specific antigens. These mutant antigens can be referred to as "cancer neoantigens" Ito, et al., Cancer Neoantigens: A Promising Source of Immunogens for Cancer Immunotherapy. *J Clin Cell Immunol*, 6:322 (2015) doi: 10.4172/2155-9899.1000322. Neoantigen-based cancer vaccines have the potential to induce more robust and specific anti-tumor T-cell responses compared with conventional shared-antigen-targeted vaccines. Recent developments in genomics and bioinformatics, including massively parallel sequencing (MPS) and epitope prediction algorithms, have provided a major breakthrough in identifying and selecting neoantigens.

Methods of identifying, selecting, and validating neoantigens are known in the art. See, for example, Ito, et al., Cancer Neoantigens: A Promising Source of Immunogens for Cancer Immunotherapy. *J Clin Cell Immunol*, 6:322 (2015) doi:10.4172/2155-9899.1000322, which is specifically incorporated by reference herein in its entirety. For example, as discussed in Ito, et al., a non-limiting example of identifying a neoantigen can include screening, selection, and optionally validation of candidate immunogens. First, the whole genome/exome sequence profile is screened to identify tumor-specific somatic mutations (cancer neoantigens) by MPS of tumor and normal tissues, respectively. Second, computational algorithms are used for predicting the affinity of the mutation-derived peptides with the patient's own HLA and/or TCR. The mutation-derived peptides can serve as antigens for the compositions and methods disclosed herein. Third, synthetic mutated peptides and wild-type peptides can be used to validate the immunogenicity and specificity of the identified antigens by in vitro T-cell assay or in vivo immunization.

III. Methods of Making Nanocages

The disclosed nanocages are generally prepared by mixing together one or more saponins, one or more lipids, one or more sterols, one or more additional adjuvants (e.g., TLR4 agonist), and optionally one or more antigens in the presence of detergent. The detergent is removed, for example by dialysis. As the detergent is removed, the components self-assemble into a dispersion of nanocages. Typically the dispersion is a monodispersion. In some embodiments, the monodispersion is of particles of approximately 40 nm.

In some embodiments, one or more of the components is in an aqueous stock solution preferably including detergent and the stock solutions are then mixed together.

Preferably the detergent is a non-ionic detergent. An exemplary non-ionic detergent is Decanoyl-N-methylglucamide (MEGA-10). In some embodiments, the non-ionic detergent is about 20% of the stock solution. The solution(s) can be heated (e.g., 60-70 degrees C.) during preparation.

The components are mixed in a ratio suitable to form nanocages when the detergent is removed. In a particular embodiment, the molar ratio is 2.5:1:10:10 of Lipid:additional adjuvant (e.g., TLR4 agonist):Sterol:Saponin. The molar ratio of any component or combination thereof can be increased or decreased by any value between about 0 and about 3.

Exemplary molar ratios are provided in Table 1.

TABLE 1

Exemplary Molar Ratios

| Lipid | Additional Adjuvant | Sterol | Saponin |
|---|---|---|---|
| 2.5 | 1 | 10 | 10 |
| 2.5 | 1 | 10 | 30 |
| 2.5 | 1 | 10 | 3 |
| 2.5 | 1 | 30 | 10 |
| 2.5 | 1 | 3 | 10 |
| 2.5 | 3 | 10 | 10 |
| 2.5 | 0.3 | 10 | 10 |
| 10 | 1 | 10 | 10 |
| 0.75 | 1 | 10 | 10 |

Thus, in some embodiments, the wherein the additional adjuvant is MPLA, the sterol is cholesterol, and the saponin is Quil A, the exemplary molar ratios can be those in Table 2.

TABLE 2

Exemplary Molar Ratios

| Lipid | MPLA | Cholesterol | Quil-A |
|---|---|---|---|
| 2.5 | 1 | 10 | 10 |
| 2.5 | 1 | 10 | 30 |
| 2.5 | 1 | 10 | 3 |
| 2.5 | 1 | 30 | 10 |
| 2.5 | 1 | 3 | 10 |
| 2.5 | 3 | 10 | 10 |
| 2.5 | 0.3 | 10 | 10 |
| 10 | 1 | 10 | 10 |
| 0.75 | 1 | 10 | 10 |

In some embodiments, the components are mixed in the following sequence: sterol, lipid, additional adjuvant (e.g., TLR4 agonist), and saponin.

In particular embodiments, the nanocages include cholesterol as the sterol, DPPC as the lipid, MPLA as the TLR4 agonist, Quil-A as the saponin, or any combination thereof. In particular embodiments, the nanocages include cholesterol as the sterol, DPPC as the lipid, MPLA as the TLR4 agonist, and Quil-A as the saponin. In even more particular embodiments, the nanocages include a molar ratio 2.5:1:10:10—DPPC:MPLA:Cholesterol:Quil-A. This embodiment is also referred to herein as "saponin-MPLA nanoparticles" and "saponin-MPLA NP."

Once mixed, the solution can be allowed to equilibrate, for example, for 2 hours to overnight.

Next, the detergent is removed. In some embodiments, the detergent is removed by dialysis against an aqueous solution. In a particular embodiment, 10 k MWCO dialysis cassettes are used and a PBS dialysis buffer is changed about two times a day for about 4 or 5 days.

Once the detergent is removed the remaining nanocage solution can be sterile filtered using, for example, a 0.2 μm filter.

The nanocages can be purified, for example from loose components such as free additional adjuvant (e.g., TLR4 agonist), by chromatography, for example Fast Protein Liquid Chromatograph (FPLC). Suitable columns include Sephacryl S-500 HR or a similar SEC column.

Preferably, few or no liposomes or micelles are formed. However, certain preparations may yield a small fraction of worm-like micelles with a main fraction containing cage-like particles. If liposomes and/or micelles are formed during the preparation, the nanocages can be selected or separated from the liposomes and/or micelles, for example during purification.

Size/morphology can be measured by dynamic light scattering (DLS) and negative-stain TEM can be used to compare batch-to-batch homogeneity.

Antigen can be added in the presence of detergent. In such embodiments, antigen is present in solution with the other components of the nanocages, and can be incorporated into the structure of nanocages during self-assembly, when detergent is removed.

In some embodiments, antigen is not included in solution with the other components of the nanocages in the presence detergent. Antigen can be added after the detergent is removed, and thus after self-assembly is complete. In such embodiments, it is believed that the antigen will remain free and untethered or unincorporated in the nanocage.

IV. Formulations

A. Pharmaceutical Compositions

Pharmaceutical compositions including nanocage adjuvants, antigens, and the combination thereof are provided. Pharmaceutical compositions can be for administration by parenteral (intramuscular, intraperitoneal, intravenous (IV), intradermal, or subcutaneous injection), or transmucosal (nasal, vaginal, rectal, or sublingual) routes of administration or using bioerodible inserts and can be formulated in dosage forms appropriate for each route of administration.

In some embodiments, the compositions are administered systemically, for example, by intravenous or intraperitoneal administration, in an amount effective for delivery of the compositions to targeted cells.

Most typically, the compositions are administered by intramuscular, intradermal, subcutaneous, or intravenous injection or infusion, or by intranasal delivery.

In certain embodiments, the compositions are administered locally, for example by injection directly into a site to be treated. In some embodiments, the compositions are injected or otherwise administered directly to one or more tumors. Typically, local injection causes an increased localized concentration of the compositions which is greater than that which can be achieved by systemic administration.

In some embodiments, the compositions are delivered by using a catheter or syringe. Other means of delivering such compositions include using infusion pumps (for example, from Alza Corporation, Palo Alto, Calif.) or incorporating the compositions into polymeric implants (see, for example, P. Johnson and J. G. Lloyd-Jones, eds., Drug Delivery Systems (Chichester, England: Ellis Horwood Ltd., 1987), which can effect a sustained release of the composition to the immediate area of the implant.

As further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired.

An exemplary dosage range for antigen and adjuvant components of a vaccine are about 10 μg to about 500 μg of antigen and about 10 μg to about 1000 μg of adjuvant. In some embodiments, the dosage range of the antigen is between about 10 ng and about 500 μg, or about 10 ng 100 μg.

Adjuvant dosages can also be determined based on activity or units. For example, concentration of the nanocages (e.g., saponin-MPLA) can be quantified by measuring the sterol (e.g., cholesterol) content of the purified products (sigma MAK043). The sterol (e.g., cholesterol) quantification is then referred to as units of activity. In some embodiments, this value is further multiplied by the mass ratio of saponin:sterol (e.g., QuilA:cholesterol) to get an estimated saponin (e.g., Quil-A) content. In some embodiments, the unit dosage of a nanocage adjuvant is between about 1 U and about 10 U, or between about 2 U and about 7 U, or between about 2.5 U and about 5 U.

1. Formulations for Parenteral Administration

In a preferred embodiment the nanocage adjuvant, the antigen, or a combination thereof are administered in an aqueous solution, by parenteral injection.

The formulation can be in the form of a suspension or emulsion. In general, pharmaceutical compositions are provided including an effective amount of the adjuvant and optionally include pharmaceutically acceptable diluents, preservatives, solubilizers, emulsifiers, adjuvants and/or carriers. Such compositions can include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80 also referred to as polysorbate 20 or 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate.

The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Formulations for Topical and Mucosal Administration

The adjuvants and/or antigens can be applied topically. Topical administration can include application to the lungs (pulmonary), nasal, oral (sublingual, buccal), vaginal, or rectal mucosa.

Compositions can be delivered to the lungs while inhaling and traverse across the lung epithelial lining to the blood stream when delivered either as an aerosol or spray dried particles having an aerodynamic diameter of less than about 5 microns.

A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent® nebulizer (Mallinckrodt Inc., St. Louis, Mo.); the Acorn® II nebulizer (Marquest Medical Products, Englewood, Colo.); the Ventolin® metered dose inhaler (Glaxo Inc., Research Triangle Park, N.C.); and the Spinhaler® powder inhaler (Fisons Corp., Bedford, Mass.). Nektar, Alkermes and Mannkind all have inhalable insulin powder preparations approved or in clinical trials where the technology could be applied to the formulations described herein.

Formulations for administration to the mucosa will typically be spray dried drug particles, which may be incorporated into a tablet, gel, capsule, suspension or emulsion. Standard pharmaceutical excipients are available from any formulator.

B. Immunogenic Compositions

The adjuvants disclosed herein can be used in immunogenic compositions and as components in vaccines. Typically, immunogenic compositions disclosed herein include an adjuvant, an antigen, or a combination thereof. When administered to a subject in combination, the adjuvant and antigen can be administered in separate pharmaceutical compositions, or they can be administered together in the same pharmaceutical composition.

When present in the same pharmaceutical composition, or administered in combination, an adjuvant and an antigen can be referred to as a vaccine.

V. Methods of Use

The disclosed compositions including a nanocage adjuvant alone or in combination with an antigen can be administered in an effective amount to induce, increase, or enhance an immune response. Immune response typically refers to responses that induce, increase, or perpetuate the activation or efficiency of innate or adaptive immunity.

The compositions can also be used to promote tolerance, e.g., to an allergen or autoimmune antigen.

The composition can be delivered parenterally (e.g., by subcutaneous, intradermal, or intramuscular injection) through the lymphatics, or by systemic administration through the circulatory system (e.g., by intravenous injection or infusion). In some embodiments, a nanocage adjuvant and an antigen are administered in the same manner or route. In other embodiments, the different compositions are administered in two or more different manners or routes.

In some embodiments, the compositions are delivered non-systemically. In some embodiments, at least the adjuvant alone or in combination with antigen is delivered locally. In some embodiments, the compositions are delivered by subcutaneous injection. In some embodiments, the composition is administered at a site adjacent to or leading to one or more lymph nodes which are close to the site in need of an immune response (i.e., close to a tumor or site of infection). In some embodiments, the composition is injected into the muscle.

In some embodiments, the composition is administered in multiple doses at various locations throughout the body. The composition can also be administered directly to a site in need of an immune response (e.g., a tumor or site of infection).

In some embodiments, particularly those for the treatment of cancer and some infections, the nanocage adjuvant is administered without administering an antigen. It is believed that the nanocage adjuvant can still increase immune response to, for example endogenous tumor antigens or microbial antigens, without administering any further antigens to the subject.

A. Methods of Increasing an Immune Response

The immune response can be induced, increased, or enhanced by the composition compared to a control. In some embodiments, a nanocage adjuvant including an additional adjuvant such as a TLR4 agonist is administered to a subject in need thereof in an effective amount to increase an antigen-specific antibody response (e.g., IgG, IgG2a, IgG1, or a combination thereof), increase a response in germinal centers (e.g., increase the frequency of germinal center B cells, increase frequencies and/or activation T follicular helper (Tfh) cells, increase B cell presence or residence in dark zone of germinal center or a combination thereof), increase plasmablast frequency, increase inflammatory cytokine expression (e.g., IL-6, IFN-γ, IFN-α, IL-1β, TNF-α, CXCL10 (IP-10), or a combination thereof), increase drainage of antigen from the injection site, increase antigen accumulation in the lymph nodes, increase lymph node permeability, increase lymph flow, increase antigen-specific B cell antigen uptake in lymph nodes, increase a humeral response beyond the proximal lymph node, increase diffusion of antigen into B cell follicles, or a combination thereof.

The control can be, for example, no adjuvant or another adjuvant. Thus, in some embodiments, the disclosed nanocage adjuvants including an additional adjuvant such as a TLR4 agonist that can increase an immune response in a subject relative to, for example, Addavax, Alum, ISCOMATRIX®, ASO1B, or another adjuvant.

The disclosed nanocage adjuvant can be used, for example, to induce an immune response, when administering the antigen alone or in combination with an alternative adjuvant is ineffectual. In some embodiments, the nanocage adjuvant may reduce the dosage of adjuvant, antigen, or both required to induce, increase, or enhance an immune response; or reduce the time needed for the immune system to respond following administration.

Nanocage adjuvants may be administered as part of prophylactic vaccines or immunogenic compositions which confer resistance in a subject to subsequent exposure to infectious agents, or as part of therapeutic vaccines, which can be used to initiate or enhance a subject's immune response to a pre-existing antigen, such as a viral antigen in a subject infected with a virus or with cancer.

The desired outcome of a prophylactic or therapeutic immune response may vary according to the disease or condition to be treated, or according to principles well known in the art. For example, an immune response against an infectious agent may completely prevent colonization and replication of an infectious agent, affecting "sterile immunity" and the absence of any disease symptoms. However, a vaccine against infectious agents may be considered effective if it reduces the number, severity or duration of symptoms; if it reduces the number of individuals in a population with symptoms; or reduces the transmission of an infectious agent. Similarly, immune responses against cancer, allergens or infectious agents may completely treat a disease, may alleviate symptoms, or may be one facet in an overall therapeutic intervention against a disease.

B. Tolerance

The compositions and methods disclosed herein may also be used to promote tolerance. Tolerogenic therapy aims to induce immune tolerance where there is pathological or undesirable activation of the normal immune response. Such embodiments may also include co-administration of an immunosuppressive agent such as rapamycin.

Tolerogenic vaccines deliver antigens with the purpose of suppressing immune responses (e.g., induce or increase a suppressive immune response) and promoting robust long-term antigen-specific immune tolerance. For example, Incomplete Freund's Adjuvant (IFA) mixed with antigenic peptides stimulates Treg proliferation (and/or accumulation) and IFA/Insulin peptide prevents type I diabetes onset in susceptible mice, though this approach is ineffective in reversing early onset type I diabetes (Fousteri, G., et al., 53:1958-1970 (2010)). The compositions and methods disclosed herein are also useful for controlling the immune response to an antigen. For example, in some embodiments, the compositions are used as part of a tolerizing vaccine.

An exemplary composition typically contains an antigen, or a nucleic acid encoding an antigen as in DNA vaccines, and a nanocage adjuvant. The antigen, for example, a self-antigen, depends on the disease to be treated, and can be determined by one of skill in the art. Exemplary self-antigens and other tolerizing antigens are discussed in more detail above. Adjuvant and antigen can be administered in an amount effective to, for example, increase immunosuppression.

C. Diseases to Be Treated

1. Infectious Diseases

The compositions are useful for treating acute or chronic infectious diseases. Thus, the compositions can be administered for the treatment of local or systemic viral infections, including, but not limited to, immunodeficiency (e.g., HIV), papilloma (e.g., HPV), herpes (e.g., HSV), encephalitis, influenza (e.g., human influenza virus A), and common cold (e.g., human rhinovirus) viral infections. For example, pharmaceutical formulations including the composition can be administered topically to treat viral skin diseases such as herpes lesions or shingles, or genital warts. The composition can also be administered to treat systemic viral diseases, including, but not limited to, AIDS, influenza, the common cold, or encephalitis.

Representative infections that can be treated, include but are not limited to infections cause by microorganisms including, but not limited to, *Actinomyces, Anabaena, Bacillus, Bacteroides, Bdellovibrio, Bordetella, Borrelia, Campylobacter, Caulobacter, Chlamydia, Chlorobium, Chromatium, Clostridium, Corynebacterium, Cytophaga, Deinococcus, Escherichia, Francisella, Halobacterium, Heliobacter, Haemophilus*, Hemophilus influenza type B (HIB), *Histoplasma, Hyphomicrobium, Legionella, Leishmania, Leptspirosis, Listeria*, Meningococcus A, B and C, *Methanobacterium, Micrococcus, Myobacterium, Mycoplasma, Myxococcus, Neisseria, Nitrobacter, Oscillatoria,* Prochloron, *Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus,* and *Treponema, Vibrio, Yersinia, Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Plasmodium vivax, Trypanosoma brucei, Entamoeba histolytica, Toxoplasma gondii, Trichomonas vaginalis* and *Schistosoma mansoni.*

In some embodiments, the type of disease to be treated or prevented is a chronic infectious disease caused by a bacterium, virus, protozoan, helminth, or other microbial pathogen that enters intracellularly.

In particular embodiments, infections to be treated are chronic infections cause by a hepatitis virus, a human immunodeficiency virus (HIV), a human T-lymphotrophic virus (HTLV), a herpes virus, an Epstein-Barr virus, or a human papilloma virus.

2. Cancer

The compositions may be used for treating cancer, by for example, stimulating or enhancing an immune response in host against the cancer. The types of cancer that may be treated with the provided compositions and methods include, but are not limited to, the following: bladder, brain, breast, cervical, colo-rectal, esophageal, kidney, liver, lung, nasopharangeal, pancreatic, prostate, skin, stomach, uterine, ovarian, testicular and hematologic.

Malignant tumors which may be treated are classified herein according to the embryonic origin of the tissue from which the tumor is derived. Carcinomas are tumors arising from endodermal or ectodermal tissues such as skin or the epithelial lining of internal organs and glands. Sarcomas, which arise less frequently, are derived from mesodermal connective tissues such as bone, fat, and cartilage. The leukemias and lymphomas are malignant tumors of hematopoietic cells of the bone marrow. Leukemias proliferate as single cells, whereas lymphomas tend to grow as tumor masses. Malignant tumors may show up at numerous organs or tissues of the body to establish a cancer.

The compositions can be administered as an immunogenic composition or as part of vaccine, such as prophylactic vaccines, or therapeutic vaccines, which can be used to initiate or enhance a subject's immune response to a pre-existing antigen, such as a tumor antigen in a subject with cancer.

The desired outcome of a prophylactic or therapeutic immune response may vary according to the disease, according to principles well known in the art. Similarly, immune responses against cancer, may alleviate symptoms, or may be one facet in an overall therapeutic intervention against a disease. For example, administration of the composition may reduce tumor size, or slow tumor growth compared to a control. The stimulation of an immune response against a cancer may be coupled with surgical, chemotherapeutic, radiologic, hormonal and other immunologic approaches in order to affect treatment.

3. Subjects in Need of Tolerance

The compositions that increase tolerance disclosed herein can be used to inhibit immune-mediated tissue destruction for example in a setting of inflammatory responses, autoimmune and allergic diseases, and transplant rejection.

a. Inflammatory and Autoimmune Disorders

In certain embodiments, the disclosed compositions are used to treat an inflammatory response or autoimmune disorder in a subject. For example, the disclosed methods can be used to prophylactically or therapeutically inhibit, reduce, alleviate, or permanently reverse one or more symptoms of an inflammatory response or autoimmune disorder. An inflammatory response or autoimmune disorder can be inhibited or reduced in a subject by administering to the subject an effective amount of a composition in vivo, or cells modulated by the composition ex vivo.

Representative inflammatory responses and autoimmune diseases that can be inhibited or treated include, but are not limited to, rheumatoid arthritis, systemic lupus erythematosus, alopecia areata, ankylosing spondylitis, antiphospholipid syndrome, autoimmune Addison's disease, autoimmune hemolytic anemia, autoimmune hepatitis, autoimmune inner ear disease, autoimmune lymphoproliferative syndrome (alps), autoimmune thrombocytopenic purpura (ATP), Bechet's disease, bullous pemphigoid, cardiomyopathy, celiac sprue-dermatitis, chronic fatigue syndrome immune deficiency, syndrome (CFIDS), chronic inflammatory demyelinating polyneuropathy, cicatricial pemphigoid, cold agglutinin disease, Crest syndrome, Crohn's disease, Dego's disease, dermatomyositis, dermatomyositis-juvenile, discoid lupus, essential mixed cryoglobulinemia, fibromyalgia-fibromyositis, grave's disease, guillain-barre, hashimoto's thyroiditis, idiopathic pulmonary fibrosis, idiopathic thrombocytopenia purpura (ITP), Iga nephropathy, insulin dependent diabetes (Type I), juvenile arthritis, Meniere's disease, mixed connective tissue disease, multiple sclerosis, myasthenia gravis, pemphigus vulgaris, pernicious anemia, polyarteritis nodosa, polychondritis, polyglancular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, sarcoidosis, scleroderma, Sjogren's syndrome, stiff-man syndrome, Takayasu arteritis, temporal arteritis/giant cell arteritis, ulcerative colitis, uveitis, vasculitis, vitiligo, and Wegener's granulomatosis.

b. Transplant Rejection

In another embodiment, the disclosed compositions and methods can be used prophylactically or therapeutically to reduce or inhibit graft rejection or graft verse host disease. Transplant rejection occurs when a transplanted organ or tissue is not accepted by the body of the transplant recipient. Typically rejection occurs because the immune system of the recipient attacks the transplanted organ or tissue. The disclosed methods can be used to promote immune tolerance of the transplant or graft by the receipt by administering to the subject an effective amount of a composition in vivo, or cells modulated by the composition ex vivo.

i. Transplants

The transplanted material can be cells, tissues, organs, limbs, digits or a portion of the body, for example the human body. The transplants are typically allogenic or xenogenic. The disclosed compositions are administered to a subject in an effective amount to reduce or inhibit transplant rejection. The compositions can be administered systemically or locally by any acceptable route of administration. In some embodiments, the compositions are administered to a site of transplantation prior to, at the time of, or following transplantation. In one embodiment, compositions are administered to a site of transplantation parenterally, such as by subcutaneous injection.

In other embodiments, the compositions are administered directly to cells, tissue or organ to be transplanted ex vivo. In one embodiment, the transplant material is contacted with the compositions prior to transplantation, after transplantation, or both.

In other embodiments, the compositions are administered to immune tissues or organs, such as lymph nodes or the spleen.

The transplant material can also be treated with enzymes or other materials that remove cell surface proteins, carbohydrates, or lipids that are known or suspected of being involved with immune responses such as transplant rejection.

(a) Cells

Populations of any types of cells can be transplanted into a subject. The cells can be homogenous or heterogenous. Heterogeneous means the cell population contains more than one type of cell. Exemplary cells include progenitor cells such as stem cells and pluripotent cells which can be harvested from a donor and transplanted into a subject. The cells are optionally treated prior to transplantation as mention above.

(b) Tissues

Any tissue can be used as a transplant. Exemplary tissues include skin, adipose tissue, cardiovascular tissue such as veins, arteries, capillaries, valves; neural tissue, bone marrow, pulmonary tissue, ocular tissue such as corneas and lens, cartilage, bone, and mucosal tissue. The tissue can be modified as discussed above.

(c) Organs

Exemplary organs that can be used for transplant include, but are not limited to kidney, liver, heart, spleen, bladder, lung, stomach, eye, tongue, pancreas, intestine, etc. The organ to be transplanted can also be modified prior to transplantation as discussed above.

One embodiment provides a method of inhibiting or reducing chronic transplant rejection in a subject by administering an effective amount of the composition to inhibit or reduce chronic transplant rejection relative to a control.

ii. Graft-Versus-Host Disease (GVHD)

The disclosed compositions and methods can be used to treat graft-versus-host disease (GVHD) by administering an effective amount of the composition to alleviate one or more symptoms associated with GVHD. GVHD is a major complication associated with allogeneic hematopoietic stem cell transplantation in which functional immune cells in the transplanted marrow recognize the recipient as "foreign" and mount an immunologic attack. It can also take place in a blood transfusion under certain circumstances. Symptoms of GVD include skin rash or change in skin color or texture, diarrhea, nausea, abnormal liver function, yellowing of the skin, increased susceptibility to infection, dry, irritated eyes, and sensitive or dry mouth.

In another embodiment, the disclosed compositions and methods for inducing or perpetuating a suppressive immune response can be used prophylactically or therapeutically to suppress allergies and/or asthma and/or inflammation. Allergies and/or asthma and/or inflammation can be suppressed, inhibited or reduced in a subject by administering to the subject an effective amount of a composition that promotes an immune suppressive immune response or tolerance as described above.

D. Combination Therapies

In some embodiments, the compositions are administered in further combination with one or more additional therapeutic agents. The agents can be administered in the same or separate pharmaceutical composition from the adjuvant, antigen, or combination thereof.

In some embodiments, the compositions are administered in combination with a conventional therapeutic agent used for treatment of the disease or condition being treated. Conventional therapeutics agents are known in the art and can be determined by one of skill in the art based on the disease or disorder to be treated. For example, if the disease or condition is cancer, the compositions can be co-administered with a chemotherapeutic drug; or if the disease or condition is a bacterial infection, the compositions can be co-administered with an antibiotic.

When administered as a cancer vaccine, the disclosed compositions may be administered in combination with a checkpoint inhibitor (PD1, CTLA4, TIM3, etc.).

E. Treatment Regimens

The nanocage adjuvants alone or more typically in combination with an antigen can be administered as a vaccine that includes a first ("prime") and optionally one or more ("boost") administrations. Thus in some embodiments, a vaccine is administered 2, 3, 4, or more times, for example, 1, 2, 3, 4, 5, 6, 7, 8, 9, 10, 11, 12, 13, 14, or 15 days, weeks, months, or years apart.

VI. Kits

Dosage units and stocks of lyophilized nanocage adjuvant alone or in combination with antigen, as well as dosage units and stocks of nanocage adjuvant alone or in combination with antigen in a pharmaceutically acceptable carrier for shipping and storage and/or administration are also provided, and can form part of a kit, for example a vaccination kit.

Components of the kit may be packaged individually and can be sterile. In some embodiments, a pharmaceutically acceptable carrier containing an effective amount of nanocage adjuvant alone or in combination with antigen is shipped and stored in a sterile vial. The sterile vial may contain enough nanocage adjuvant alone or in combination with antigen for one or more doses. In some embodiments, the adjuvant and antigen are in separate containers, which may be combined before administration.

In some embodiments, the adjuvant, the antigen, or both are in a dried or lyophilized form. The kit may include a pharmaceutical carrier that can be used to resuspend the adjuvant, antigen, or combination thereof. In some embodiments, the kit includes adjuvant and/or antigen, or a combination of adjuvant and antigen already suspended in a pharmaceutical carrier.

Nanocage adjuvant alone or in combination with antigen may be shipped and stored in an amount or volume suitable for administration, or may be provided in a concentrated form that is diluted prior to administration. In another embodiment, a pharmaceutically acceptable carrier containing an effective amount of nanocage adjuvant alone or in combination with antigen can be shipped and stored in a syringe.

Kits can also contain syringes of various capacities or vessels with deformable sides (e.g., plastic vessels or plastic-sided vessels) that can be squeezed to force a liquid composition out of an orifice. The size and design of the syringe will depend on the route of administration. For example, in one embodiment, a syringe for administering the compositions locally, may be capable of accurately delivering a smaller volume. Larger syringes, pumps and/or catheters can also be provided. Any of the kits can include instructions for use.

EXAMPLES

Example 1: Saponin-MPLA Can Form a Nanoparticle Adjuvant

Materials and Methods

Saponin-MPLA Nanoparticle Synthesis

Materials: DPPC (Avanti 850355); Cholesterol (Avanti 700000, ovine wool); Quil-A Lyophilized Saponin (InvivoGen vac-quil); MEGA-10 (N-Decanoyl-N-methylglucamine, Sigma D6277); MPLA (PHAD) (Avanti 699800P)

Nanocage Preparation: 20% MEGA-10 stock was prepared in sterile mQ-H2O. A 20 mg/mL solution of cholesterol was prepared in 20% MEGA-10 by heating 60 to 70° C. in a water bath. A 20 mg/mL solution of DPPC was prepared in 20% MEGA-10 by heating 60 to 70° C. in a water bath. A 5 mg/ml solution of PHAD was prepared in 20% MEGA-10 by heating to 60 to 70° C. in a water bath. A 100 mg/mL Quil-A saponin solution in sterile mQH2O. The components in the following molar ratio 2.5:1:10:10-DPPC:MPLA:Cholesterol:Quil-A and in the following sequence: Cholesterol, DPPC, MPLA, Quil-A. PBS was added so that cholesterol is at a final concentration of 1 mg/ml.

The solution was allowed to equilibrate for 2 hours to overnight, and dialyze against 1xPBS for 4-5 days using 10 k MWCO dialysis cassettes, changing dialysis buffer 2 times per day.

Following dialysis, the material was collected, sterile filtered using 0.2 μm filter, and purified by FPLC using a Sephacryl S-500 HR or similar SEC column.

This formulation produced a small fraction of worm-like micelles and a main fraction containing monodisperse 40 nm cage-like particles. The 40 nm cage-like particle fractions were used for in vivo studies.

Saponin Nanoparticle Synthesis

Materials: DPPC (Avanti 850355); Cholesterol (Avanti 700000, ovine wool); Quil-A Lyophilized Saponin (InvivoGen vac-quil); MEGA-10 (N-Decanoyl-N-methylglucamine, Sigma D6277)

Nanocage Preparation: 20% MEGA-10 stock was prepared in sterile mQ-H2O. A 20 mg/mL solution of cholesterol was prepared in 20% MEGA-10 by heating 60 to 70° C. in a water bath. A 20 mg/mL solution of DPPC was prepared in 20% MEGA-10 by heating 60 to 70° C. in a water bath. A 100 mg/mL Quil-A saponin solution in sterile mQH2O. The components in the following molar ratio 5:10:10-DPPC:Cholesterol:Quil-A and in the following sequence: Cholesterol, DPPC, Quil-A. PBS was added so that cholesterol is at a final concentration of 1 mg/ml.

The solution was allowed to equilibrate for 2 hours to overnight, and dialyze against 1xPBS for 4-5 days using 10 k MWCO dialysis cassettes, changing dialysis buffer 2 times per day.

Following dialysis, the material was collected, sterile filtered using 0.2 µm filter, and purified by FPLC using a Sephacryl S-500 HR or similar SEC column.

This formulation produced a small fraction of worm-like micelles and a main fraction containing monodisperse 40 nm cage-like particles. The 40 nm cage-like particle fractions were used for in vivo studies.

Particle Characterization

Size/morphology was measured by DLS and negative-stain TEM to ensure batch-to-batch homogeneity, the prepared product being a monodisperse population at ~40 nm in diameter.

Raw-Blue TLR4 Reporter Assay

Cells were incubated with a top dilution of 1 µg/ml of free MPLA, 10 U of Saponin-MPLA NP (10 µg/ml saponin and 1 µg/ml MPLA) and 10 U of Saponin NP (10 µg/ml saponin).

Humeral Immune Response Assay

Balb/C mice were immunized with 5 µg CRM197 (diphtheria toxin antigen) along with either 5 U of saponin nanoparticles (5 µg of saponin) or 5 U of saponin-MPLA nanoparticles (5 µg of saponin and 0.5 µg of synthetic MPLA). CRM197-specific antibody responses were assessed 16 days post prime.

Germinal Center Response Assays

Balb/C mice were immunized with 5 µg CRM197 (diphtheria toxin antigen) along with either 5 U of saponin nanoparticles (5 µg of saponin) or 5 U of saponin-MPLA nanoparticles (5 µg of saponin and 0.5 g of synthetic MPLA). The draining lymph nodes were stained for germinal center B cell markers (B220+, GL7+, CD38−, CD4−) and analyzed through a flow cytometer.

Results

Iscomatrix-like adjuvants such as ISCOMATRIX® have been shown to be effective in mice, rabbits, and non-human primates, and are thought to function via canonical inflammasome activation and subsequent release of pro-inflammatory cytokines such as IL-18 and IL-10 and (Wilson, et al., Journal of immunology. 2014; 192(7):3259-68. doi: 10.4049/jimmunol.1302011. PubMed PMID: 24610009). This mechanism is thought to be at least in part mediated by endosomal degradation and the release of NRLP3-activating cathepsin proteases into the cytosol.

Experiments were designed to determine if delivering both inflammasome priming and activating signals in the same particle could be yet another mechanism in which incorporating MPLA into Iscomatrix-like adjuvants particles may be beneficial. Saponin-cholesterol-phospholipid nanoparticles incorporating the fully-synthetic MPLA molecule phosphorylated hexa-acyl disaccharide (PHAD®) (referred to as "saponin-MPLA nanoparticles") were formed.

As in vitro experiments using bone marrow derived macrophages have demonstrated that Iscomatrix-like adjuvants are not capable of inducing inflammasome signaling without first priming with an MyD88 activator such as LPS (Wilson, et al., Journal of immunology. 2014; 192(7):3259-68. doi: 10.4049/jimmunol.1302011. PubMed PMID: 24610009; Deuwell, et al., Journal of immunology. 2011; 187(1):55-63. doi: 10.4049/jimmunol.1004114. PubMed PMID: 21613613; PMCID: 4285562), Upon testing, it was discovered that substituting up to 50% of the lipid mass fraction of an ISCOMATRIX®-like iscomatrix adjuvant formulation (referred to as "saponin nanoparticles") with MPLA to saponin-MPLA nanoparticles resulted in the successful assembly of ~40 nm nanocage structures analogous non-MPLA saponin nanoparticles. Free MPLA and non-complexed components were removed by size exclusion chromatography and purified particles were harvested for further analysis. Compared to saponin nanoparticles, incubation of RAW-Blue reporter cells along with purified saponin-MPLA nanoparticles resulted in effective TLR4 activation and demonstrated that MPLA can efficiently incorporated into the nanoparticles and remain capable of engaging TLR4 receptors (FIG. 1).

Figure 2A:
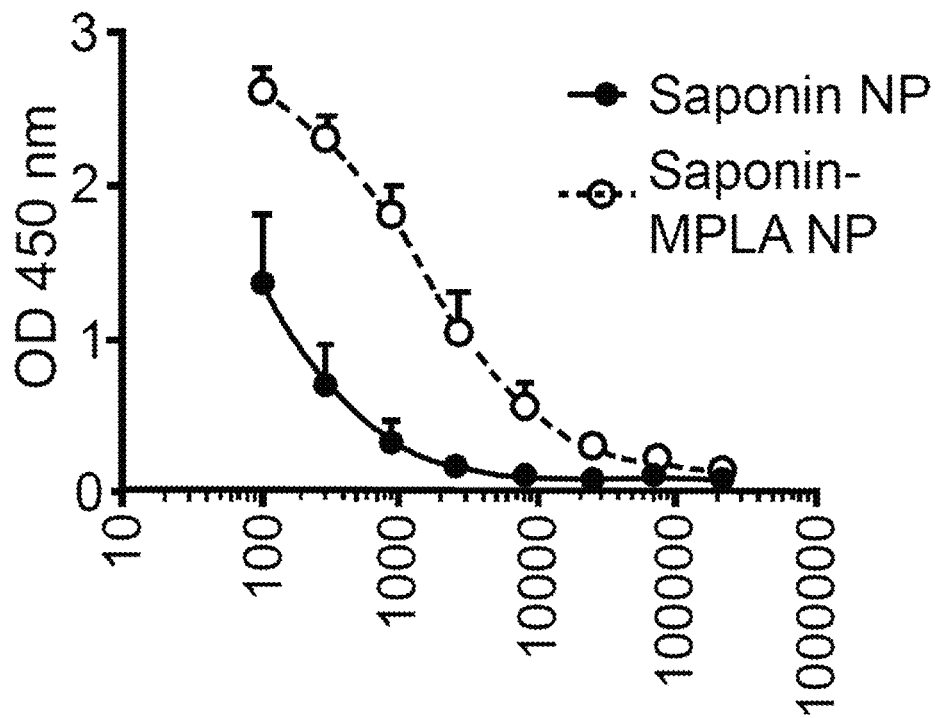
FIG. 2A is a line graph showing antigen-specific serum antibody binding curves for Saponin nanoparticles (NP) and Saponin-MPLA nanoparticles (NP) following immunization of Balb/c mice with CRM197 16 days post prime.
Figure 2B:
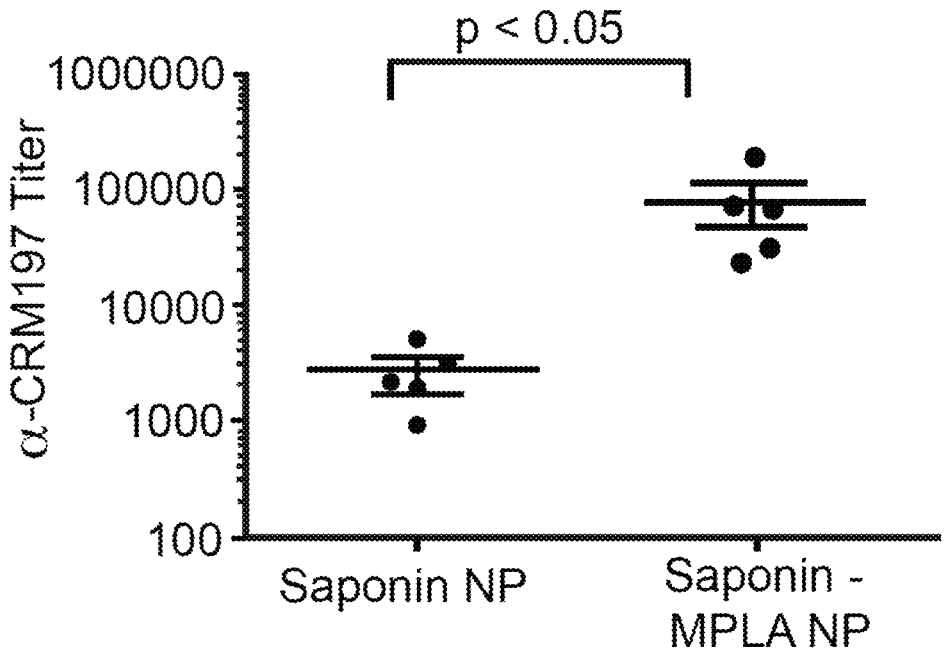
FIG. 2B is a dot plot showing CRM197-specific antibody titer (0.2 cut-off) after immunization with Saponin nanoparticles (NP) or Saponin-MPLA nanoparticles (NP).

To determine if the saponin-MPLA nanoparticles adjuvant formulation could induce humoral responses, Balb/C mice were immunized with 5 g CRM197 (diphtheria toxin antigen) along with either 5 U of saponin nanoparticles (5 µg of saponin) or 5 U of saponin-MPLA nanoparticles (5 µg of saponin and 0.5 µg of synthetic MPLA). CRM197-specific antibody responses were assessed 16 days post prime demonstrated >25-fold higher titers in mice receiving saponin-MPLA nanoparticles as compared to saponin nanoparticles (FIG. 2A-2B).

Figure 3A:
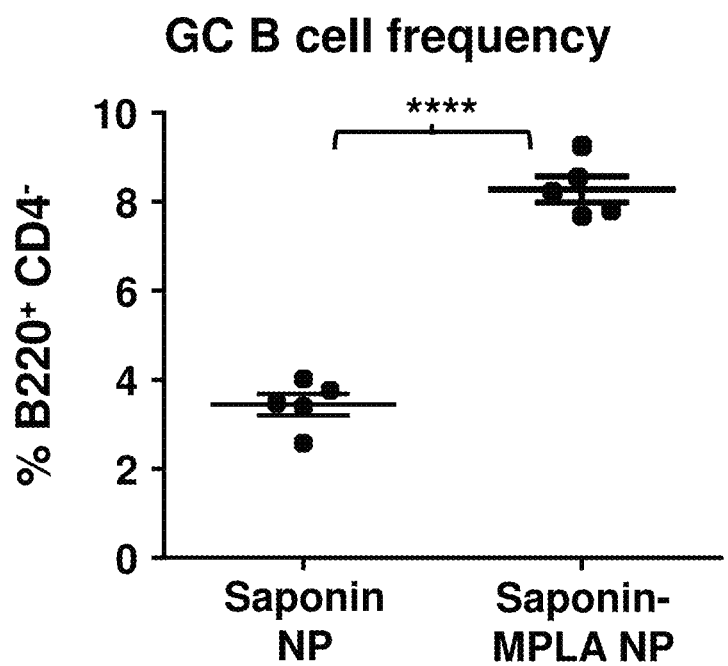
FIG. 3A is a dot plot showing quantification of CD38−GL7+ B cells in draining lymph nodes after immunization with Saponin nanoparticles (NP) or Saponin-MPLA nanoparticles (NP) and CRM197.
Figure 3B:
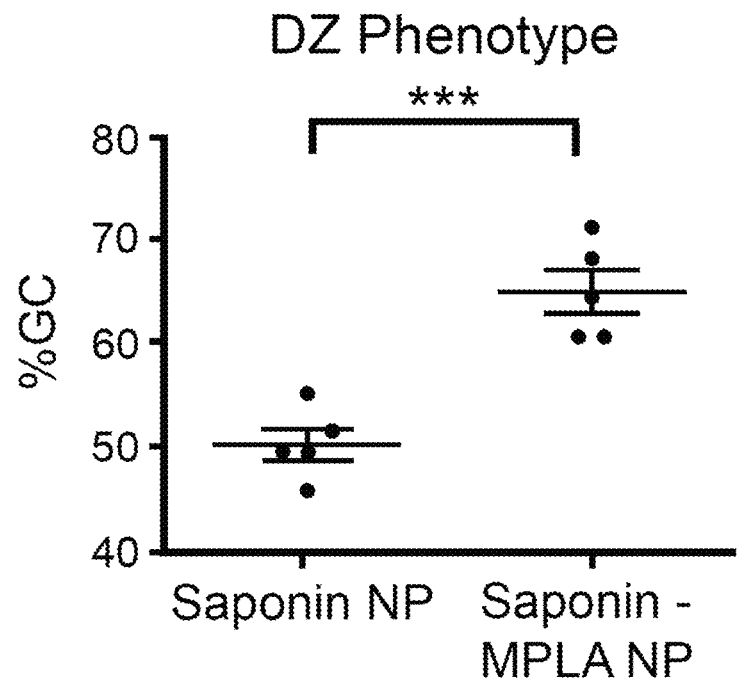
FIG. 3B is a dot plot showing quantification of $CXCR4^{hi}$ $CD86^{lo}$ dark-zone GC B cells after immunization with Saponin nanoparticles (NP) or Saponin-MPLA nanoparticles (NP) and CRM197.

As HIV vaccines will likely need to induce a substantial amount of SHM to generate broad viral neutralization (Mascola, et al., Immunological reviews. 2013; 254(1):225-44), experiments were designed to test if these adjuvants would differentially promote germinal center (GC) responses. Compared to saponin nanoparticles, saponin-MPLA nanoparticles doubled the frequency of GC B cells at the time-point tested (FIG. 3A-3B).

Figure 3C:
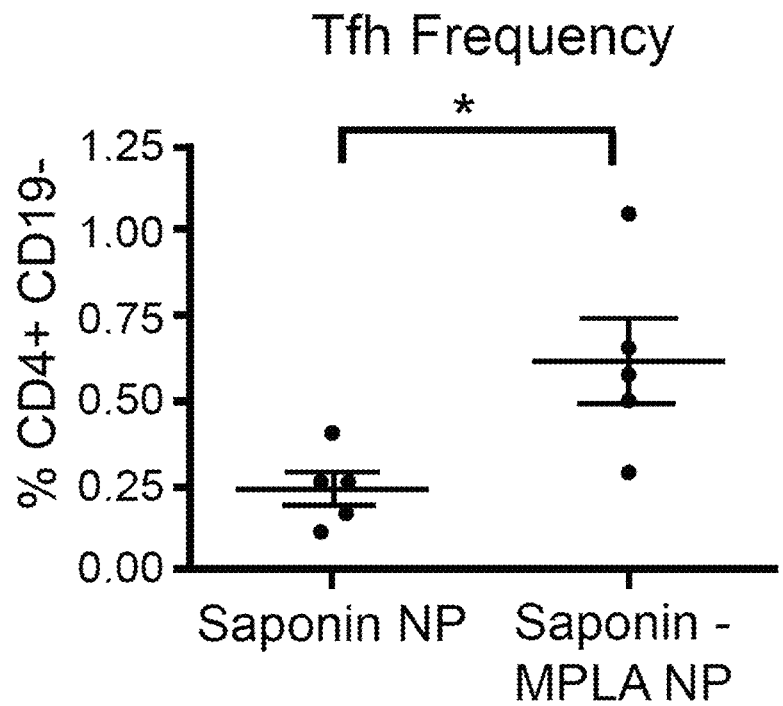
FIG. 3C is a dot plot showing quantification of $CXCR5^{hi}$ $PD1^{hi}$ T cells in the draining lymph node after immunization with Saponin nanoparticles (NP) or Saponin-MPLA nanoparticles (NP) and CRM197.
Figure 3D:
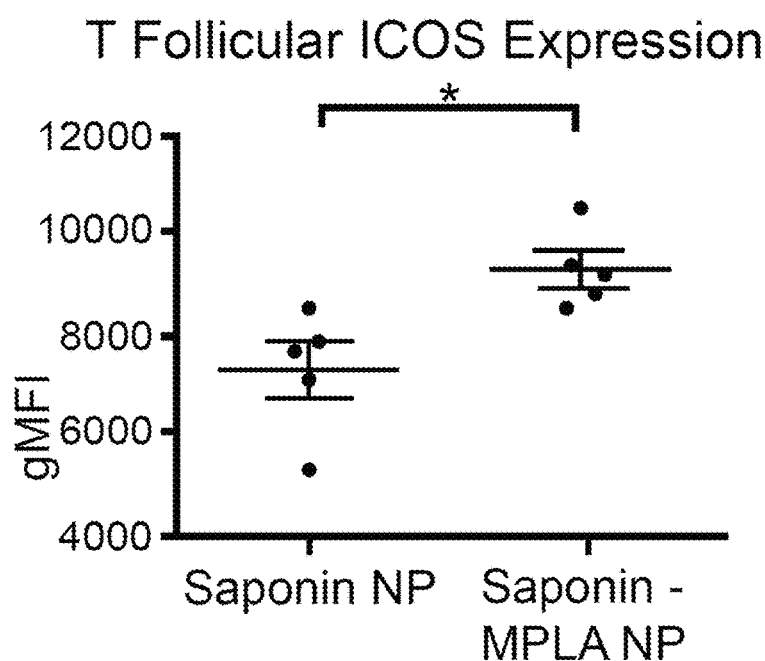
FIG. 3D is a dot plot showing ICOS expression level of T follicular helper cells after immunization with Saponin nanoparticles (NP) or Saponin-MPLA nanoparticles (NP) and CRM197.

Follicular B helper T cells (Tfh) responses are important for sustaining the GC reaction and driving high affinity antibody responses after immunization. The overall strength of Tfh help has also been shown to be important in controlling B cell residence time in the dark zone (DZ) of GCs and are thought to ultimately control the B cell proliferative program (Gitlin, et al., Nature. 2014; 509(7502):637-40. doi: 10.1038/nature13300. PubMed PMID: 24805232; Ersching, et al., Immunity. 2017; 46(6):1045-58. e6.). Saponin-MPLA nanoparticles appears to induce both greater frequencies and more potently activated Tfh cells as compared to saponin nanoparticles (FIG. 3C-3D).

Consistent with this finding, GC B cells from mice immunized saponin-MPLA nanoparticles preferentially reside in the DZ of the GC (FIG. 3B) and indicates that these cells are receiving stronger T cell help and may be proliferating at a faster rate compared to saponin nanoparticles (Gitlin, et al, Science. 2015; 349(6248):643-6. doi: 10.1126/science.aac4919. PubMed PMID: 26184917; PMCID: 4809261). Overall these results indicate that saponin-MPLA nanoparticles are a substantially more potent adjuvant compared to saponin nanoparticles.

Figure 4A:
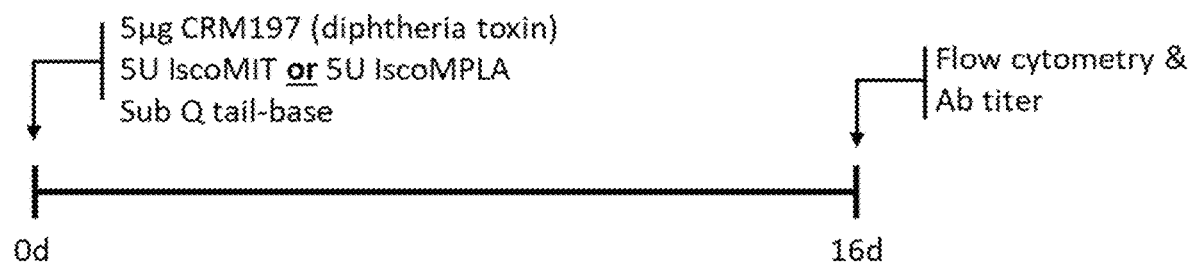
FIG. 4A is a diagram showing an experimental scheme for comparing the immunogenicity of saponin NP and saponin-MPLA NP and CRM197.
Figure 4B:
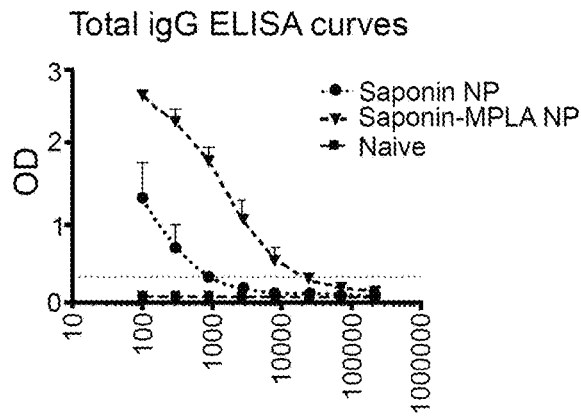
FIGS. 4B, 4D, and 4F are line graphs showing ELISA curves
Figure 4C:
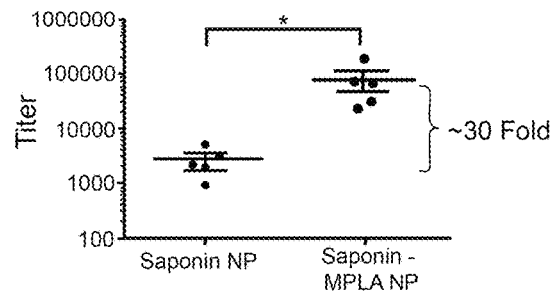
FIGS. 4C, 4E, and 4G are dot plots showing titer analysis of antigen specific total IgG (4B-4C), IgG2a (4D-4E), and IgG1 (4F-4G) of saponin NP and saponin-MPLA NP.
Figure 4D:
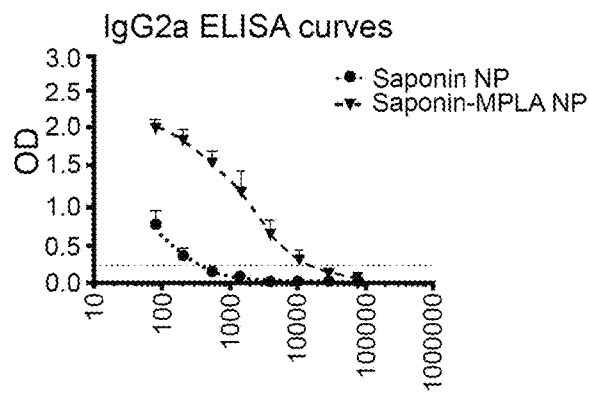
Figure 4E:
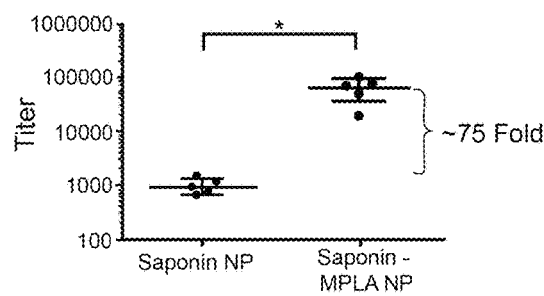
Figure 4F:
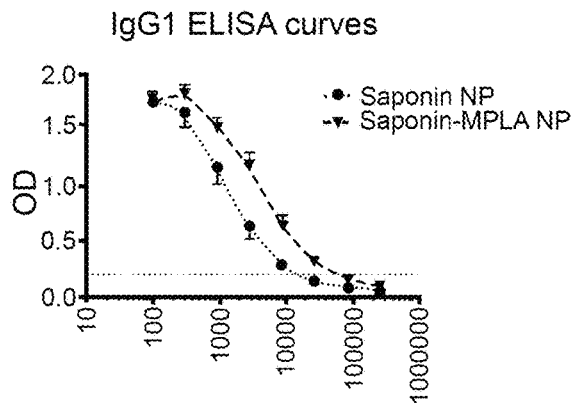
Figure 4G:
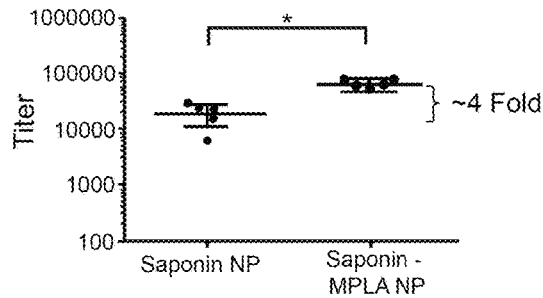

Example 2: Saponin-MPLA Nanoparticles are More Immunogenic Than Other Adjuvants Materials and Methods CRM197 Antigen Assay Age and sex matched Balb/C mice were immunized in the base of the tail with 5 µg of CRM197 (diphtheria toxin) using either 5 µg Saponin NP or 5 µg Saponin-MPLA NP. Serum was collected at day 16 for antibody analysis. The Experimental Scheme is depicted in FIG. 4A.

Adjuvant Comparison Assay

Figure 5A:
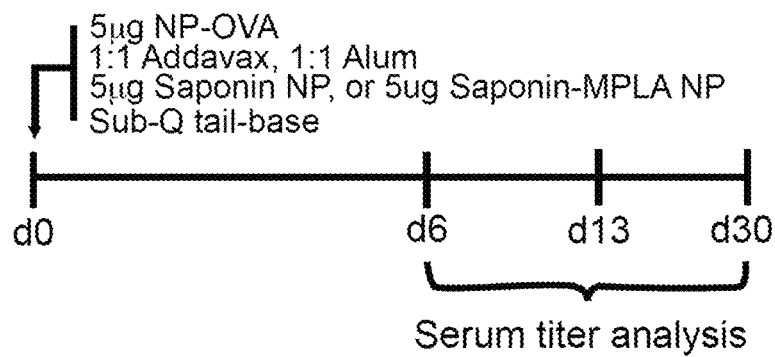
FIG. 5A is a diagram showing an experimental scheme for comparing the immunogenicity of 4-Hydroxy-3-nitrophenylacetylovalbumin (NP-OVA) when combined with Addavax, Alum, saponin NP, or saponin-MPLA NP adjuvants.

Age and sex matched Balb/C mice were immunized in the base of the tail with 5 µg of NP-OVA using either 5 µg Saponin NP, 5 µg Saponin-MPLA NP, a 1:1 dilution with Addavax or a 1:1 dilution with Alum. Serum was collected at days 6, 13, and 30 for antibody analysis. The Experimental Scheme is depicted in FIG. 5A.

Results

Results show that saponin-MPLA NP promote a significantly stronger immune response than saponin NPas measured by CRM197 antigen specific IgG, IgG2a, and IgG1. The results are illustrated in FIGS. 4B-4G, which provide raw ELISA curves (FIGS. 4A, 4C, 4E) and titer analysis (FIGS. 4B, 4D, 4F) of antigen specific total IgG (FIG. 4A, 4B), IgG2a (4C, 4D), and IgG1 (4E, 4G).

Figure 5B:
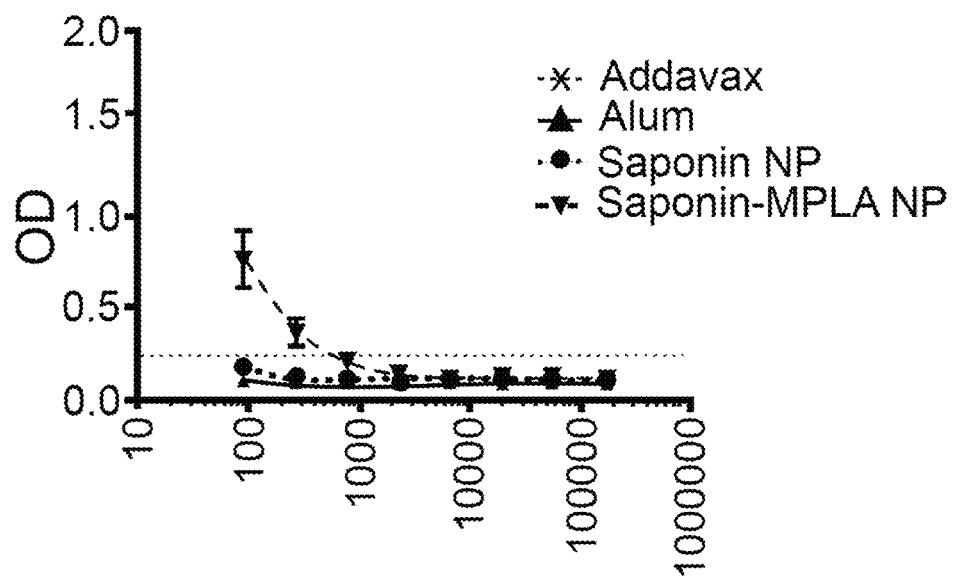
FIGS. 5B, 5C, and 5D are line graphs showing ELISA curves of antigen specific total IgG for Addavax, Alum, saponin NP, and saponin-MPLA NP at day 6 (5B), day 13 (5C), and day 30 (5D).
Figure 5C:
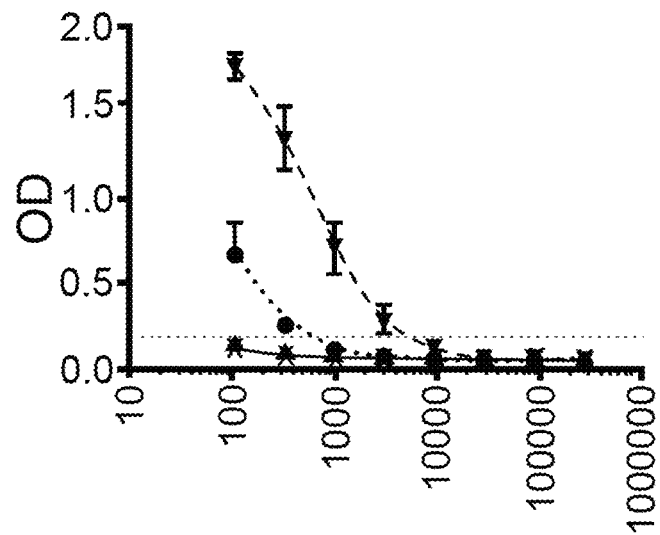
Figure 5D:
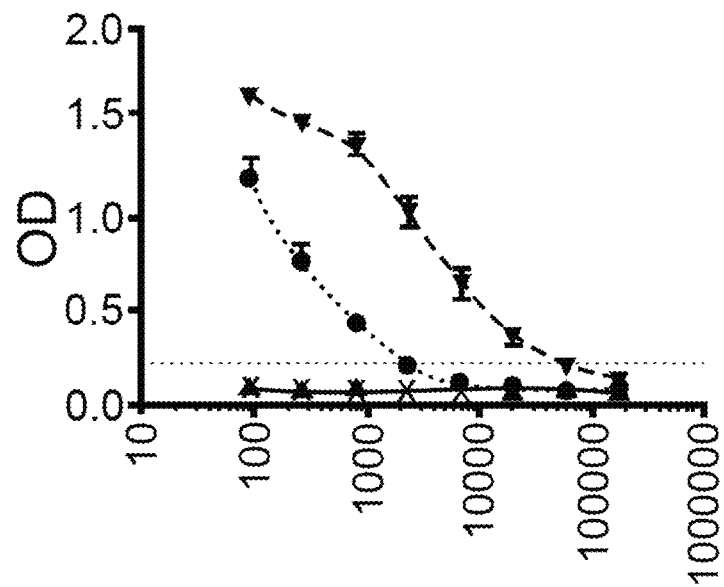

Results show that saponin-MPLA NP are significantly more immunogenic than Addavax, Alum, and saponin NP as measured by OVA antigen specific total IgG on days 6 (FIG. 5B), 13 (FIG. 5C), and 30 (FIG. 5D) after immunization.

Figure 6A:
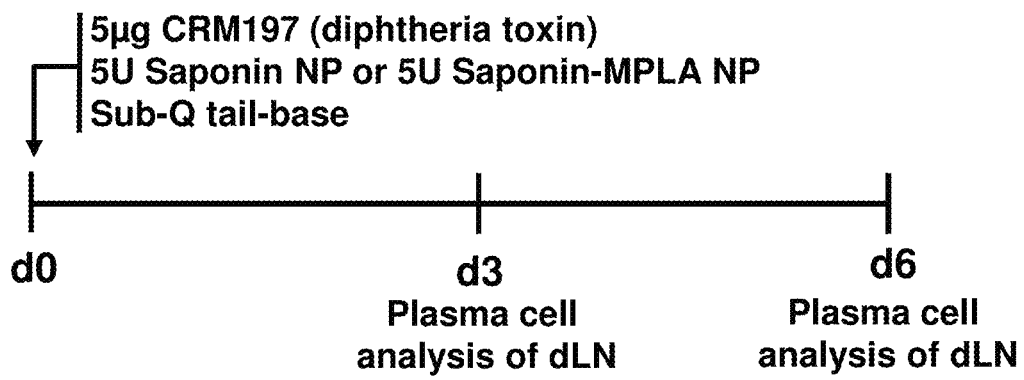
FIG. 6A is a diagram showing an experimental scheme for comparing the plasmablast frequency following immunization with and CRM197 and saponin NP or saponin-MPLA NP.

Example 3: Saponin-MPLA Nanoparticles Increase Plasmablast Frequency and Dendritic Cell Recruitment in the Draining Lymph Node Materials and Methods Plasma Cell Analysis Age and sex matched Balb/C mice were immunized in the base of the tail with 5 µg of CRM197 (diphtheria toxin) using either 5 µg Saponin NP or 5 µg Saponin-MPLA NP. Draining lymph nodes were harvested for analysis 3 and 6 days post prime. Live, CD4-, CD138+, B220$^{int}$ (plasmablasts) were quantified by flow cytometry. An Experimental Scheme is depicted in FIG. 6A.

Dendritic Cell Analysis

Age and sex matched Balb/C mice were immunized in the base of the tail with 5 µg of CRM197 (diphtheria toxin) using either 5 µg Alum or 5 µg Saponin-MPLA NP. Draining lymph nodes were harvested for analysis 4 days post immunization. Lymph node slices were stained for subcapsular sinus macrophages (CD169), dendritic cells (CD11c), and Naïve B cells (IgD)

Results

Figure 6B:
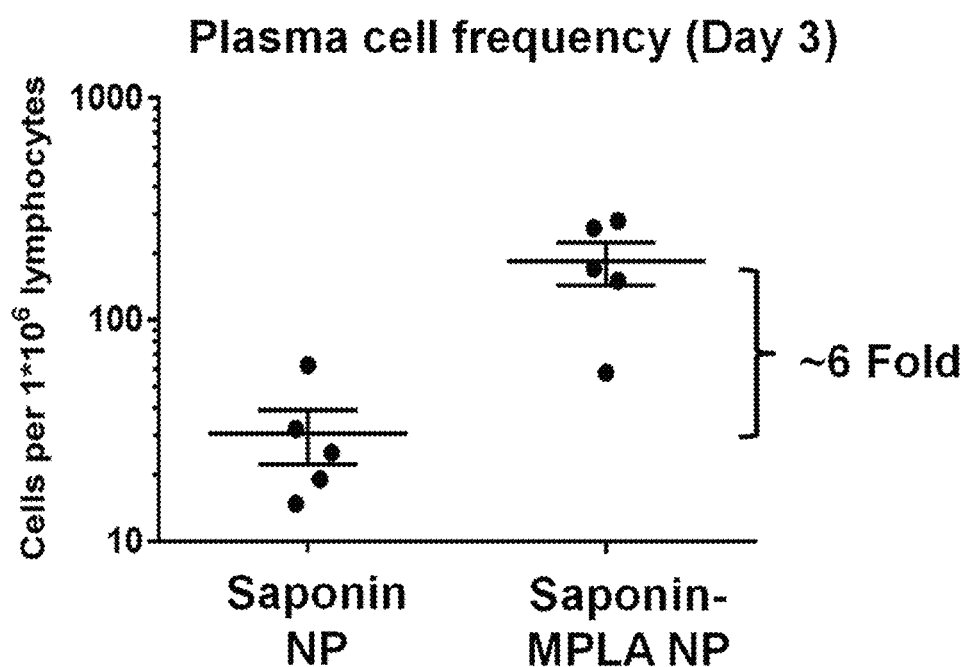
FIGS. 6B and 6C are dot plots showing quantification of CD4−, CD138+, $B220^{int}$ plasmablasts from draining lymph nodes on day 3 (6B) and day 6 (6C) post prime.
Figure 6C:
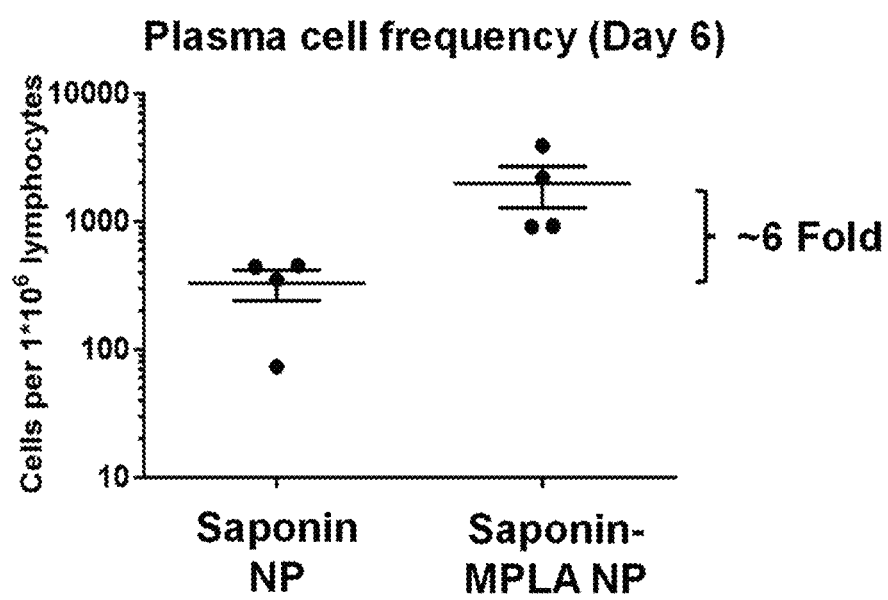

Results show that saponin-MPLA NP significantly increase the frequency of plasmablast in the draining lymph nodes on days 3 (FIG. 6B) and 6 (FIG. 6C) post immunization. Immunofluorescent analysis of lymph node slices stained for subcapsular sinus macrophages (CD169), dendritic cells (CD11c), and Naïve B cells (IgD), also shows an increase in dendritic cells in the draining lymph nodes of saponin-MPLA NP relative to alum treated animals.

Figure 7A:
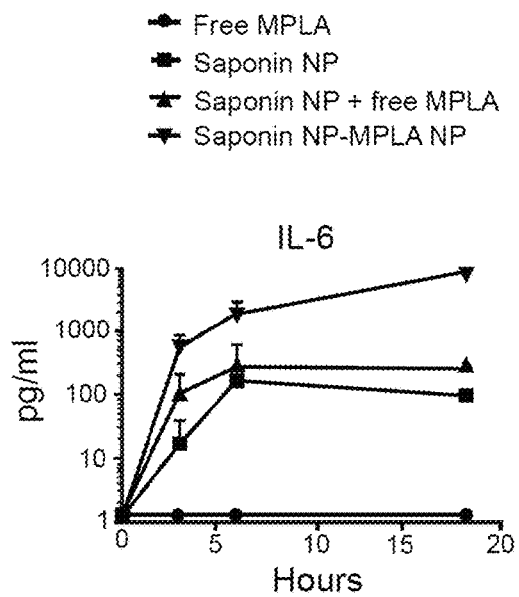
FIGS. 7A-7F are line graphs showing for pro-inflammatory cytokine expression (IL-6 (7A), IFN-γ (7B), IFN-α (7C), IL-1β (7D), TNF-α (7E), CXCL10 (IP-10) (7F)) in the draining lymph nodes of mice treated with 0.5 μg free MPLA, 5 ug Saponin NP, 5 ug Saponin NP+0.5 ug free MPLA, or 5 μg Saponin-MPLA NP at 3, 6, or 18 hours after injection.

Example 4: Saponin-MPLA NP Induce a Pro-inflammatory Cytokine Profile in the Draining Lymph Node Materials and Methods Age and sex matched Balb/C mice were immunized in the base of the tail with 0.5 g free MPLA, 5 ug Saponin NP, 5 ug Saponin NP+0.5 ug free MPLA, or 5 µg Saponin-MPLA NP. Draining lymph nodes were harvested and the cytokine profile was analyzed at 3, 6, and 18 hrs post immunization. An Experimental Scheme is depicted in FIG. 7A.

Results

Figure 7B:
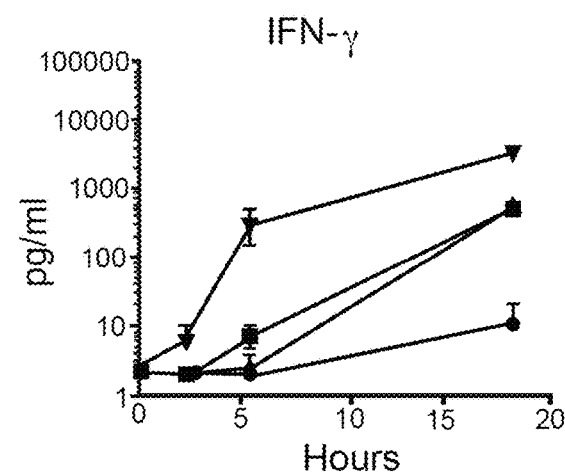
Figure 7C:
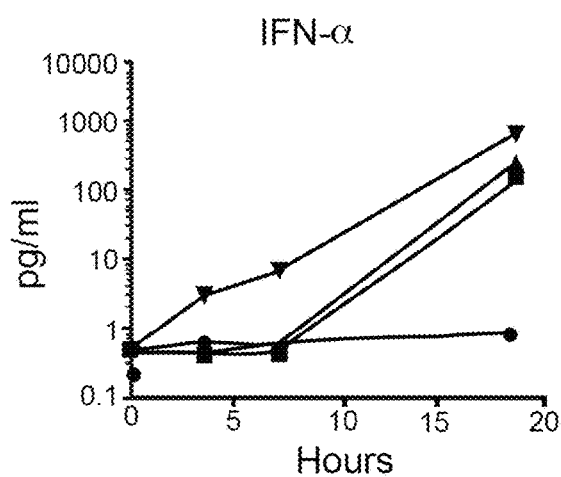
Figure 7D:
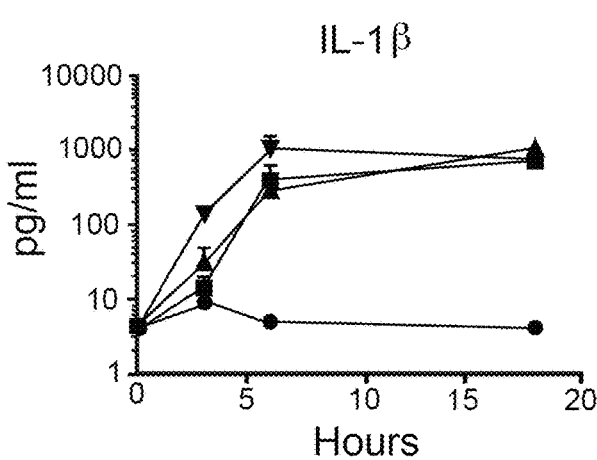
Figure 7E:
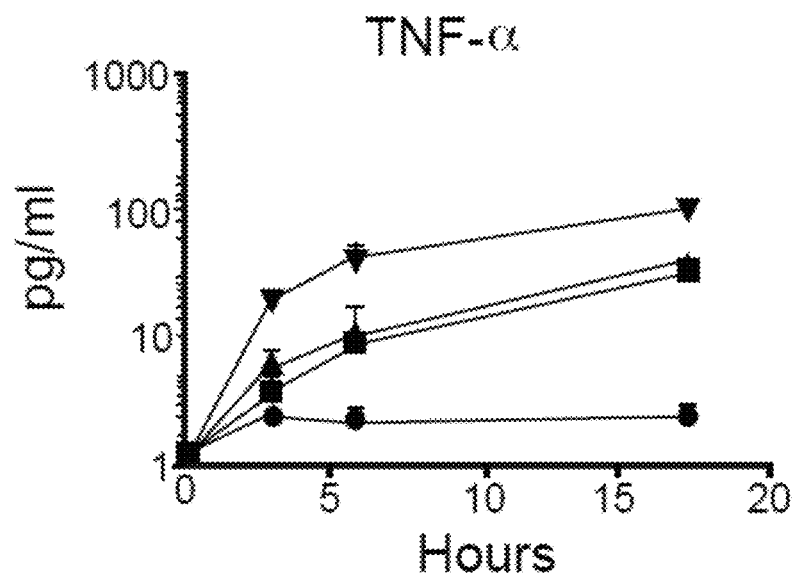
Figure 7F:
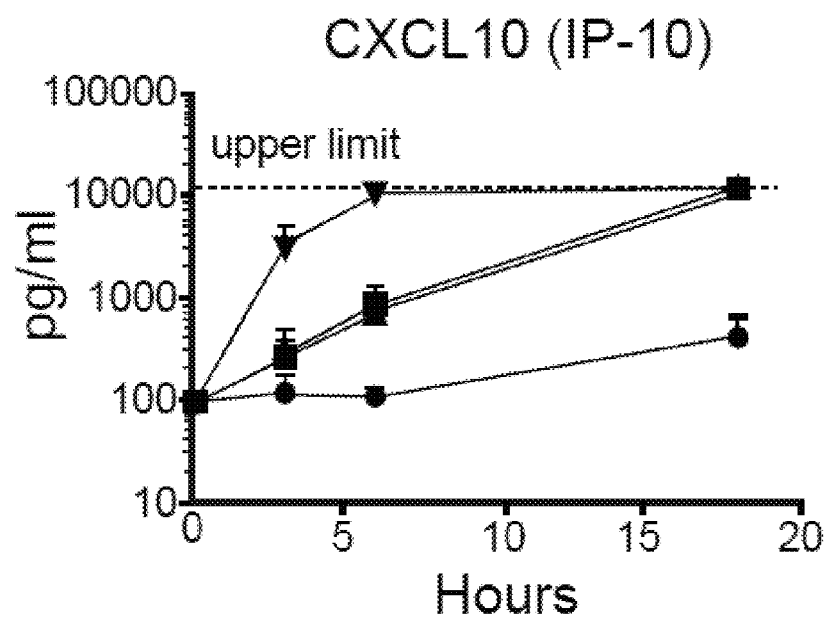

The results show that saponin-MPLA NP out performs free MPLA, saponin NP, and saponin NP+free MPLA in increasing pro-inflammatory cytokine expression including IL-6 (FIG. 7A), IFN-7 (FIG. 7B), IFN-α (FIG. 7C), IL-1β (FIG. 7D), TNF-α (FIG. 7E), and CXCL10 (IP-10) (FIG. 7F)) in the draining lymph nodes.

Figure 8A:
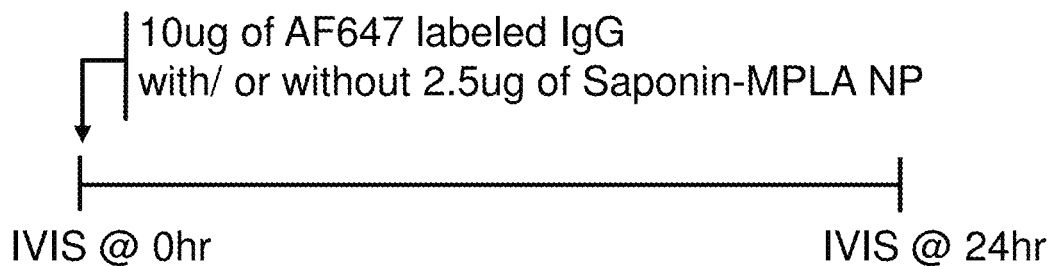
FIG. 8A is a diagram showing an experimental scheme for analyzing antigen drainage from the injection site.

Example 5: Saponin-MPLA NP Promote Antigen Drainage From the Injection Site to the Lymph Node and Increases Lymph Node Permeability Materials and Methods Antigen Drainage from the Injection Site Age and sex matched rats were injected intradermally with 10 µg of Alexa647 labeled IgG with or without 2.5 µg of Saponin-MPLA NP. An Experimental Scheme is depicted in FIG. 8A.

Antigen Drainage to the Lymph Node

Figure 9A:
FIG. 9A is a diagram showing an experimental scheme for analyzing antigen drainage to the lymph node.

Age and sex matched mice were injected at the base of tail with 20 µg of Alexa750 labeled CRM197 alone or with the specified adjuvant (20 ug CPG, 1:1 Addavax, 20 ug MPLA, 5 ug Saponin NP, 5 ug Saponin-MPLA NP). An Experimental Scheme is depicted in FIG. 9A.

Lymph Node Permeabilization

Age and sex matched Balb/C mice were injected in the base of the tail with PBS or 5 µg Saponin-MPLA NP at −6 hr. Mice were injected with a 0.1% solution of 0.2 um fluorospheres at −2 hr. Draining lymph nodes were harvested for analysis at 0 hr. Lymph node slices were stained for subcapsular sinus macrophages (CD169), lymphatic vasculature (Lyve-1), B cells (B220), and fluorescent beads. An Experimental Scheme is depicted in FIG. 9C.

Results

Figure 8B:
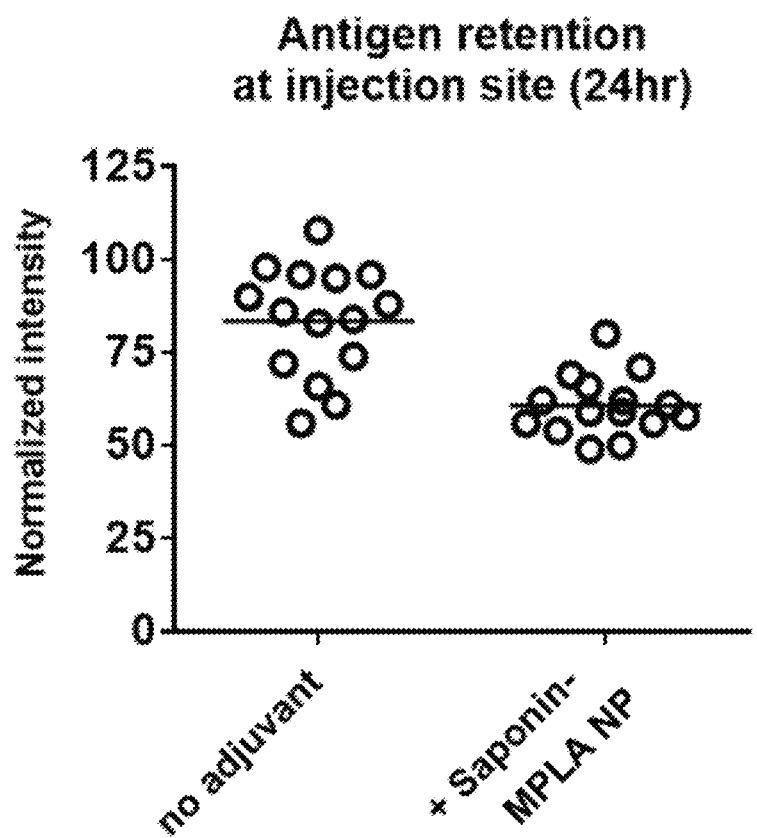
FIG. 8B is a dot plot showing quantification of fluorescence intensity at the injection site 24 hours after injection of mice with Alexa647 labeled IgG with or without saponin-MPLA NP (normalized to individual injection intensity at 0 hours).

Fluorescence quantification shows that antigen signal at the injection site is reduced in animals treated with saponin-MPLA NPs relative to no adjuvant 24 hours after injection (FIG. 8B).

Figure 9B:
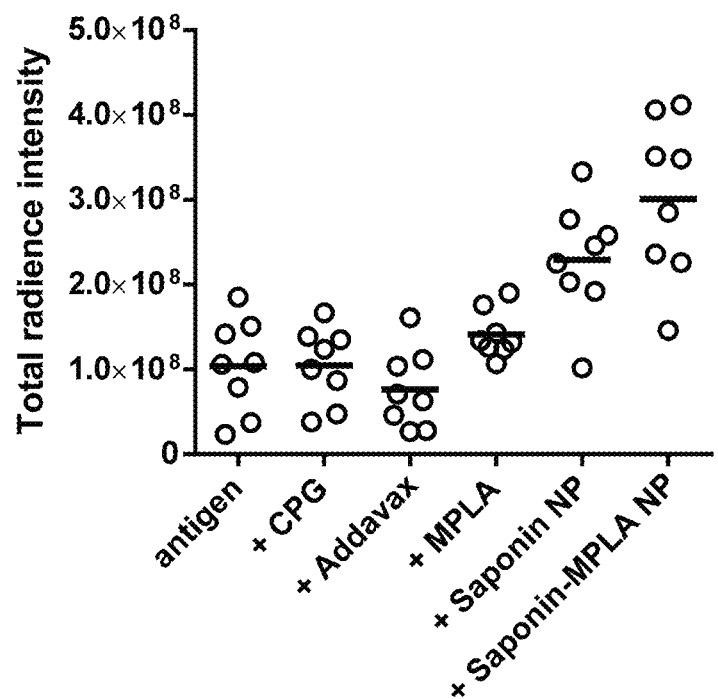
FIG. 9B is a dot plot showing quantification of 0.2 m fluorescent bead drainage into the lymph node.
Figure 9C:
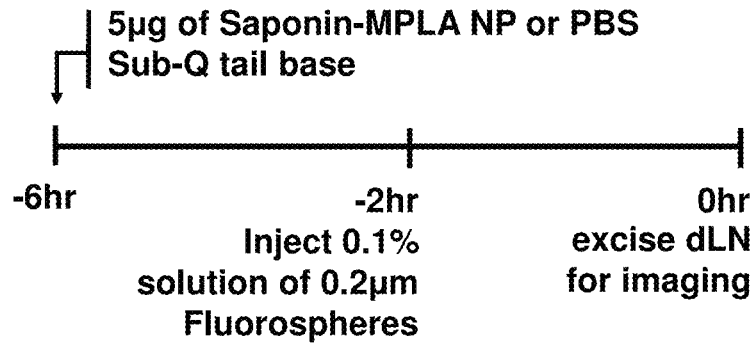
FIG. 9C is an experimental scheme for analyzing lymph node permeability. The tissue was stained for B cells (B220), CD169 (Macrophages), lymphatic vessels (Lyve-1) and fluorescent beads, and analyze by fluorescent microscopy.

Fluorescence quantification shows that antigen signal in the draining lymph nodes is increased in animals treated with saponin-MPLA NPs relative to no adjuvant 5 hours after injection (FIG. 9B).

Immunofluorescent analysis of lymph node slices stained for subcapsular sinus macrophages (CD169), lymphatic vasculature (Lyve-1), B cells (B220), and fluorescent beads evidence an increase in lymph node permeability.

Example 6: Saponin/MPLA-NP Promote Antigen-specific B Cell Antigen Uptake in Draining LN

Materials and Methods

B6 mice adoptively transferred with antigen-specific VRC01$^{gHL}$ BCR knock-in B cells were subcutaneously immunized with AlexaFluor647-tagged eOD-GT5 60mer nanoparticle antigen alone or together with TLR3 agonist (polyI:C) TLR4 agonist (MPLA), TLR9 agonist (lipid-CpG), saponin-NP or saponin/MPLA-NP.

Results

Figure 10A:
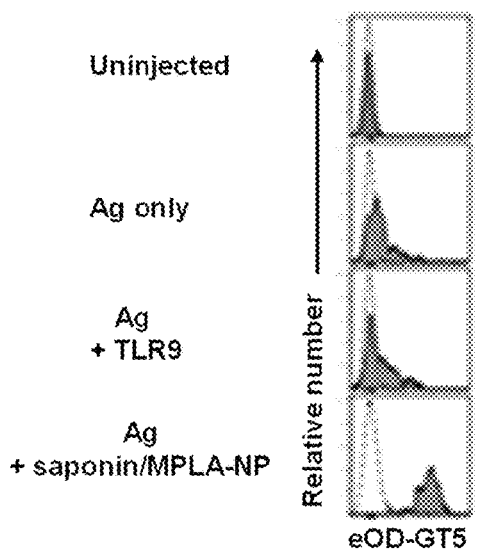
FIG. 10A is series of histograms showing comparing Ag uptake by VRC01$^{gHL}$ cells in draining LNs of uninjected mice, or 24 hours post-vaccination with AlexaFluor647-tagged eOD-GT5 60meronly, AlexaFluor647-tagged eOD-GT5 60mer+TLR9 agonist, or saponin-MPLA NP.

Ag uptake by VRC01$^{gHL}$ cells in draining lymph nodes was analyzed 24 hours post-vaccination. Non-VRC01-class B cells do not take up Ag (FIG. 10A, dotted lines). Antigen uptake by B cells was much improved in the presence of saponin/MPLA-NP (FIG. 10A, solid lines).

Figure 10B:
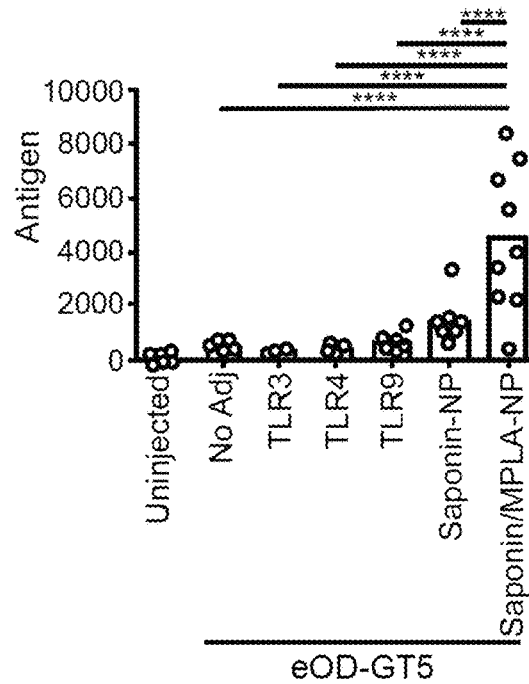
FIGS. 10B and 10C are bar graphs overlayed by dot plots showing quantification of eOD-GT5 60mer uptake (10B) and activation of antigen-specific B cells in vivo as assessed based on CCR7 expression (10C) for uninjected mice, and mice following AlexaFluor647-tagged eOD-GT5 60mer nanoparticle antigen alone or together with TLR3 agonist (polyI:C), TLR4 agonist (MPLA), TLR9 agonist (lipid-CpG), saponin-NP or saponin-MPLA NP.

FIG. 10B shows quantification of eOD-GT5 60mer uptake. Antigen uptake in vivo by B cells was much improved in the presence of saponin/MPLA-NP.

Figure 10C:
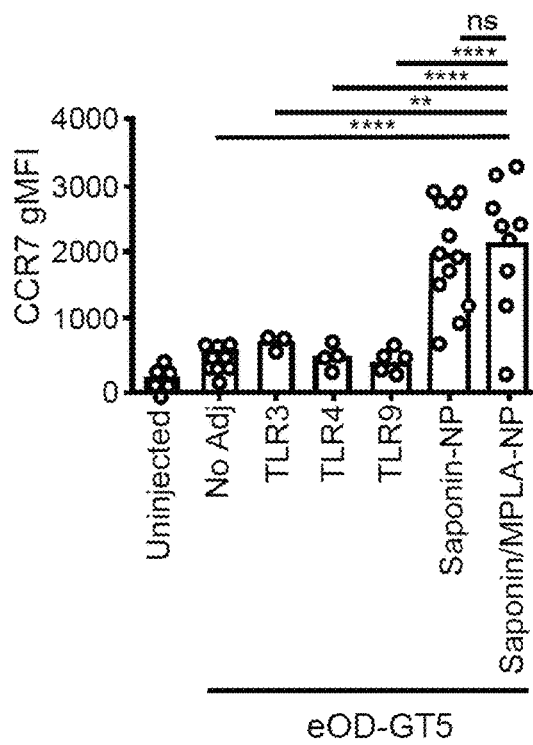

FIG. 10C shows activation of antigen-specific B cells in vivo as assessed based on CCR7 expression. Activation of antigen-specific B cells was much improved in the presence of saponin/MPLA-NP.

Immunofluorescence microscopy analysis of draining LN showed accumulation of antigen-specific VRC01$^{gHL}$ cells in the T/B border 24 h post-vaccination with the eOD-GT5 60mer together with saponin/MPLA-NP, demonstrating much improved in vivo localization of antigen-specific B cells in the presence of saponin/MPLA-NP.

Figure 10D:
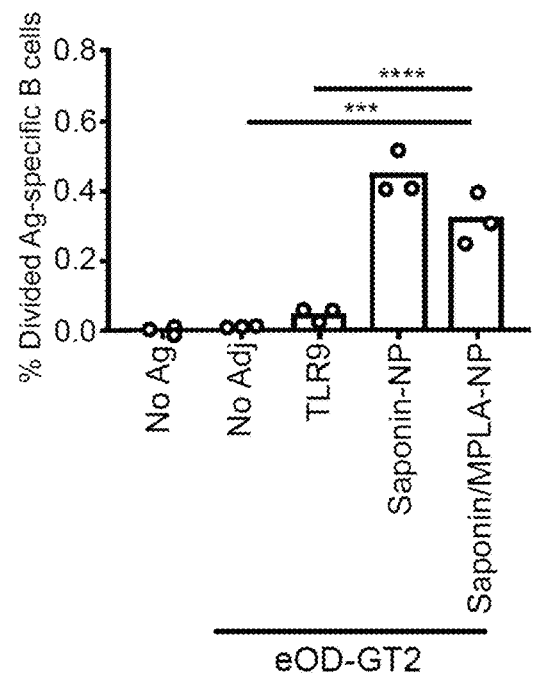
FIG. 10D is a bar graph overlayed by dot plots showing the percentage of CTV$^{lo}$ divided VRC01$^{gHL}$ cells of total B cells in the draining iLN was assessed on day 3 after subcutaneous immunization with eOD-GT2 60mer nanoparticle antigen alone or together with TLR9 agonist (lipid-CpG), saponin-NP or saponin/MPLA-NP.

B6 mice adoptively transferred with CellTrace Violet$^+$ eOD-specific VRC01$^{gHL}$ B cells subcutaneously were immunized with eOD-GT2 60mer nanoparticle antigen alone or together with TLR9 agonist (lipid-CpG), saponin-NP or saponin/MPLA-NP. The percentage of CTV$^{lo}$ divided VRC01$^{gHL}$ cells of total B cells in the draining iLN was assessed on day 3. FIG. 10D shows much improved proliferation of antigen-specific B cells in vivo in the presence of saponin/MPLA-NP.

Figure 10E:
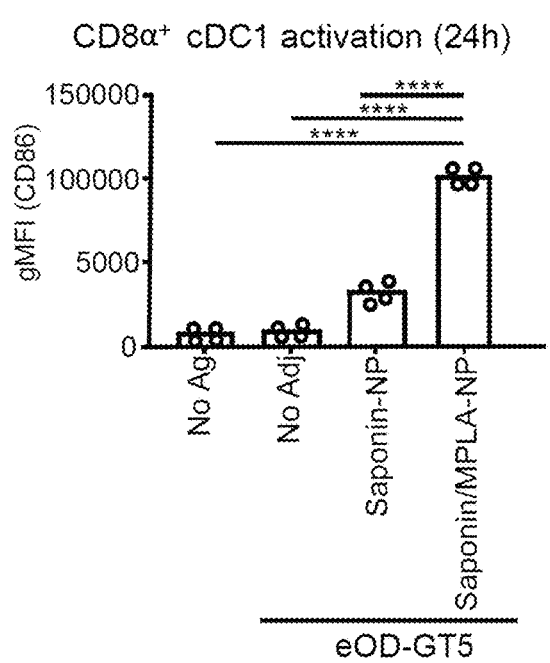
FIGS. 10E and 10F are bar graphs overlayed by dot plots showing activation of CD8α$^+$ cDC1 (10E) and CD11b$^+$ cDC2 (10F) as assessed based on CD86 expression 24 h post-immunization with eOD-GT5 60mer nanoparticle alone or together with saponin-NP or saponin/MPLA-NP.
Figure 10F:
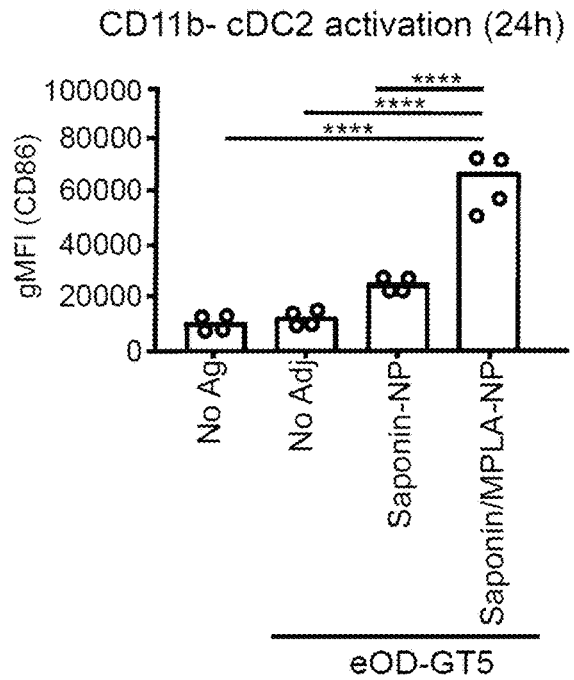

B6 mice were immunized eOD-GT5 60mer nanoparticle alone or together with saponin-NP or saponin-MPLA. Activation of CD8α$^+$ cDC1 (FIG. 10E) and CD11b$^+$ cDC2 (FIG. 10F) were assessed based on CD86 expression 24 h post-immunization, and showed much improved DC activation in vivo in the presence of saponin/MPLA-NP.

Figure 10G:
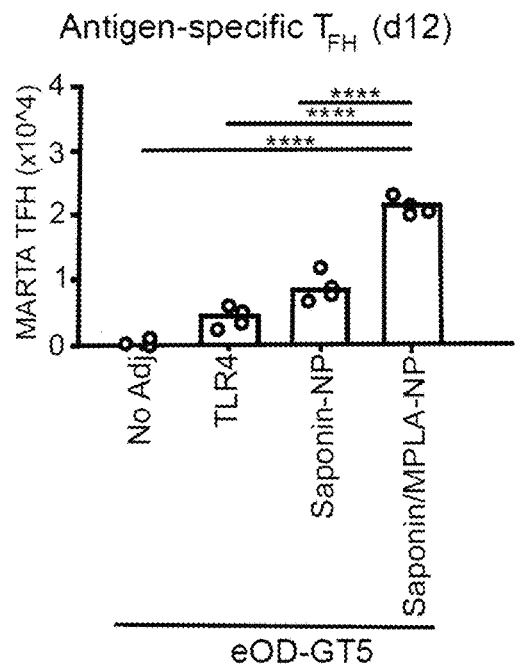
FIG. 10G is a bar graph overlayed by dot plots showing quantification of CXCR5$^{hi}$ Bcl6$^{hi}$ SMARTA T$_{FH}$ cells in the draining iLN on day 12 after immunization with eOD-GT5-gp$_{61-80}$ 60mer nanoparticle antigen alone or together with TLR4 agonist (MPLA), saponin-NP or saponin/MPLA-NP.

B6 mice adoptively transferred with LCMV gp$_{61-80}$ specific SMARTA CD4$^+$ T cells were subcutaneously immunized with eOD-GT5-gp$_{61-80}$ 60mer nanoparticle antigen alone or together with TLR4 agonist (MPLA), saponin-NP or saponin/MPLA-NP. CXCR5$^{hi}$ Bcl6$^{hi}$ SMARTA T$_{FH}$ cells in the draining iLN were enumerated on day 12. FIG. 10G shows much improved antigen-specific Tfh cell response in vivo in the presence of saponin/MPLA-NP.

Example 7: Saponin-MPLA NP Induces Potent Humoral Responses Beyond the Proximal Lymph Node

Materials and Methods

Figure 11A:
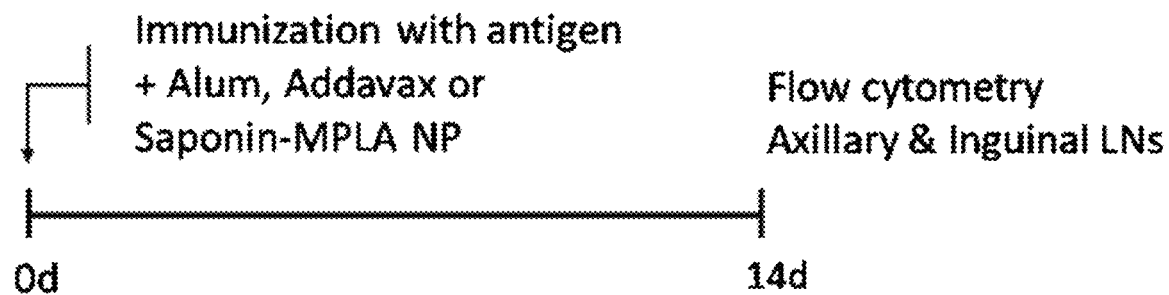
FIG. 11A is a schematic of the experiment in Example 7.

C57/bl6 mice were immunized sub-Q in the at the base of tail with adjuvant (Alum, Addavax, or Saponin-MPLA NP) along with phycoerythrin antigen. The proximal draining inguinal lymph node (iLN) and distal axillary lympn node (axLN) was harvested for analysis 2 weeks post prime. An experimental schematic is illustrated in FIG. 11A.

Results

Figure 11B:
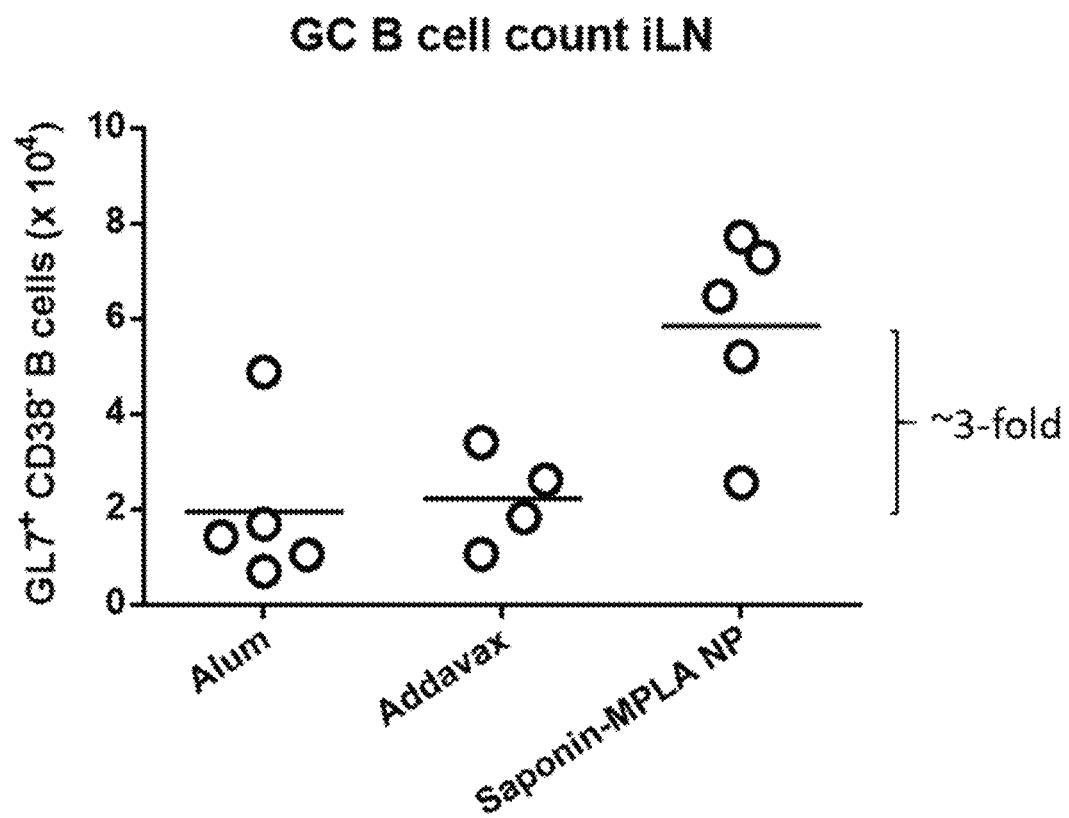
FIGS. 11B and 11C are dot plots showing quantification of the germinal center reaction (B22020+, CD4–, GL7+, CD38–) of the proximal (11B) and distal lymph nodes (11C).
Figures 11C, 12A:
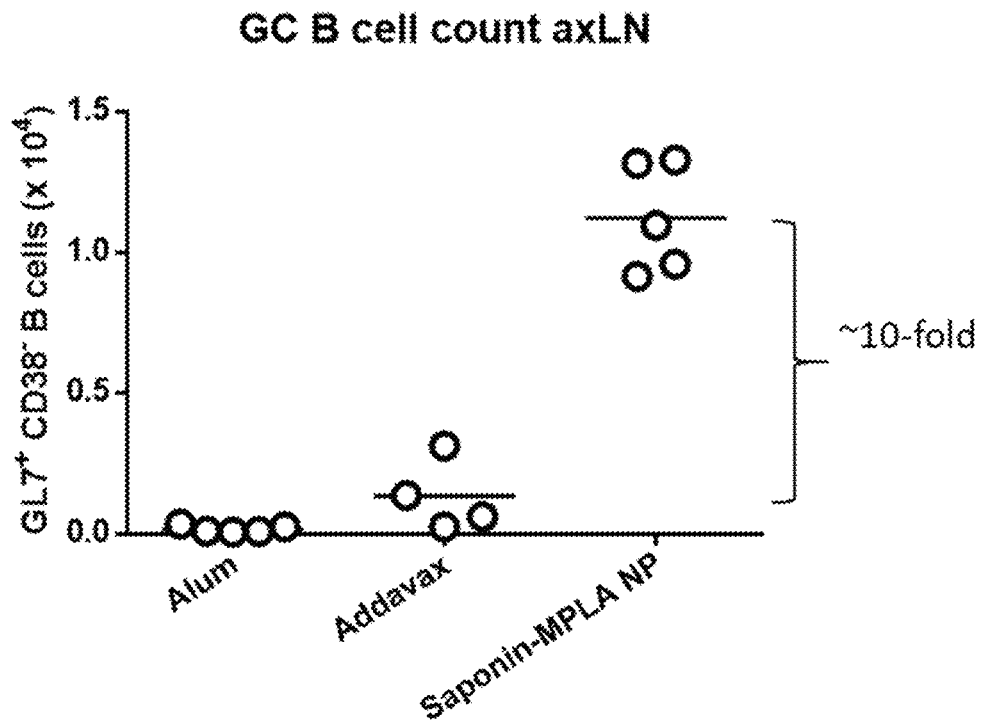
FIG. 12A is a schematic of the experiment in Example 8.

The results are illustrated in FIGS. 11B and 11C, which show quantification of the germinal center reaction (B22020+, CD4−, GL7+, CD38−) of the proximal (11B) and distal lymph nodes (11C). These results indicate that Saponin-MPLA NP induces potent humoral responses beyond the proximal lymph node.

Example 8: Saponin-MPLA NP Induces Diffusion of Antigen into B Cell Follicle

Materials and Methods

C57/bl6 mice were immunized sub-Q at the base of tail with fluorescent 70 kDa dextran along with saponin-MPLA NP or PBS. The draining inguinal lymph node was harvested for analysis 4 hours post injection. An experimental schematic is illustrated in FIG. 12A.

Results

Figure 12B:
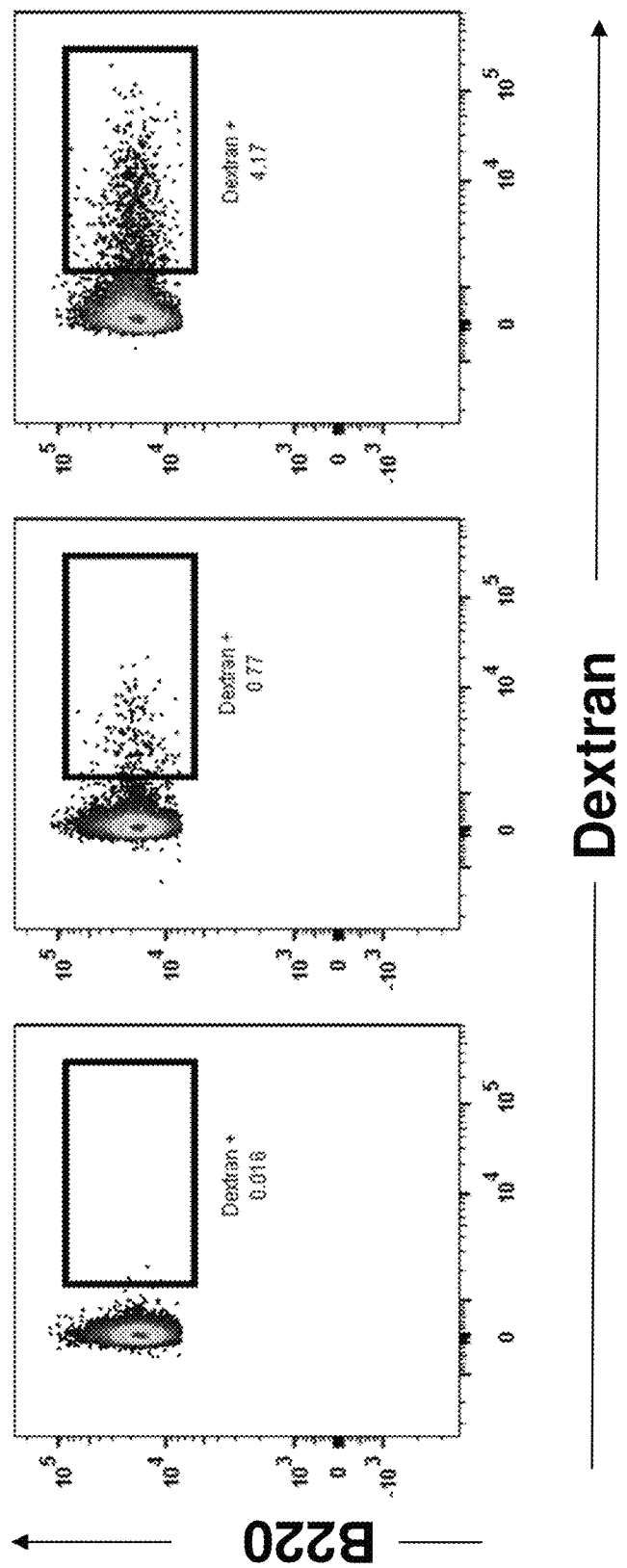
FIG. 12B is a series of scatter plots (from left-to-right: naïve, dextran+PBS, Dextran+Saponin-MPLA NP) showing representative flow cytometry data of B cell antigen capture.
Figure 12C:
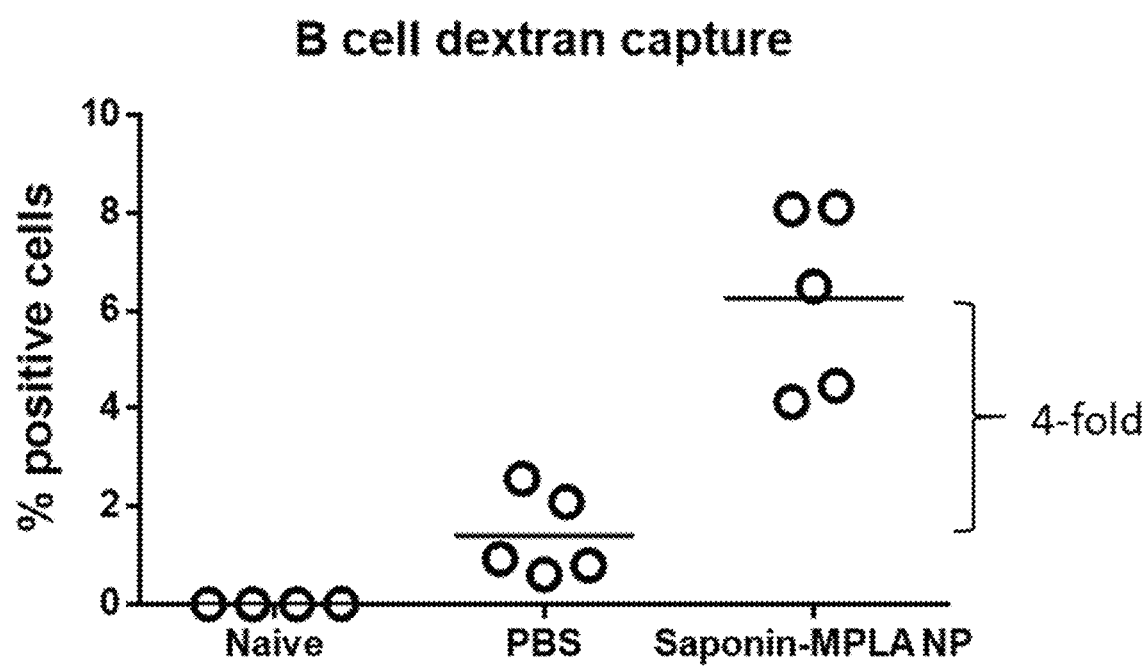
FIG. 12C is a dot plot showing quantification (% percent positive cells) of B cell antigen capture.

The results are illustrated in FIGS. 12B and 12C, which show representative flow cytometry data of B cell antigen capture (B) and quantification (C). These results indicate that Saponin-MPLA NP induces diffusion of antigen into B cell follicle.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A porous or perforated non-liposome, non-micelle nanoparticle comprising a phospholipid, a sterol, a saponin, and a TLR4 agonist lipopolysaccharide (LPS) or a lipid A derivative thereof.

2. The particle of claim 1, wherein the saponin comprises Quil A or QS-21.

3. The particle of claim 1, wherein the nanoparticle is about 30 nm to about 60 nm.

4. The particle of claim 1, wherein the phospholipid is 2-Dipalmitoyl-sn-glycero-3-phosphocholine (DPPC).

5. The particle of claim 1, wherein the lipopolysaccharide (LPS) or lipid A derivative thereof is a natural or synthetic monophosphoryl lipid A (MPLA).

6. The particle of claim 5 comprising lipid: MPLA: sterol: saponin molar ratio of 2.5:1:10:10, or a variation thereof wherein the molar ratio of lipid, MPLA, sterol, saponin or any combination thereof is increased or decreased by any value between about 0 and about 3.

7. The particle of claim 5, wherein the MPLA is natural or synthetic 4'-monophosporyl lipid A (MPLA) or 3-O-deacylated monophosphoryl lipid A (3D-MPLA).

8. The particle of claim 1, wherein the sterol is cholesterol or a derivative thereof.

9. The particle of claim 1, wherein the saponin is a natural or synthetic saponin.

10. A method of making the particle of claim 1, comprising mixing the phospholipid, sterol, saponin, and lipopolysaccharide (LPS) or a lipid A derivative thereof in an aqueous carrier comprising detergent to form a solution and removing the detergent until the phospholipid, sterol, saponin, and lipopolysaccharide (LPS) or a lipid A derivative thereof self-assemble into porous or perforated nanoparticles.

11. A pharmaceutical composition comprising a plurality of the particle of claim 1 and a pharmaceutical carrier.

12. A method of treating a subject in need thereof comprising administering the subject the pharmaceutical composition of claim 11 in an effective amount to induce an immune response against an antigen.

13. A kit comprising a plurality of the particles of claim 1 in a lyophilized or dried form, or suspended in a pharmaceutically acceptable carrier.

14. The particle of claim 1, wherein the saponin is Quil A.

15. The particle of claim 14, wherein the sterol is cholesterol, the lipopolysaccharide (LPS) or a lipid A derivative thereof is MPLA, and the phospholipid is DPPC.

16. The particle of claim 1, the saponin is QS-21.

17. The particle of claim 16, wherein the sterol is cholesterol, the lipopolysaccharide (LPS) or a lipid A derivative thereof is MPLA, and the phospholipid is DPPC.

18. A porous or perforated non-liposome, non-micelle, cage-like nanoparticle comprising a phospholipid, cholesterol, QS-21, and MPLA.

19. The pharmaceutical composition of claim 11, further comprising an antigen.

20. The pharmaceutical composition of claim 19, wherein the antigen is derived from a source selected from the group consisting of a virus, bacterium, parasite, plant, protozoan, fungus, tissue and transformed cell.

* * * * *